US012575729B2

(12) United States Patent
Sharifzadeh et al.

(10) Patent No.: US 12,575,729 B2
(45) Date of Patent: Mar. 17, 2026

(54) BIMODAL METHOD FOR DETECTION AND MEASUREMENT OF MACULAR PIGMENTS IN RETINA TISSUE

(71) Applicant: OcuScore, LLC, Lehi, UT (US)

(72) Inventors: Mohsen Sharifzadeh, Cottonwood Heights, UT (US); Jack Peterson, Elk Ridge, UT (US)

(73) Assignee: OcuScore, LLC, Lehi, UT (US)

( * ) Notice: Subject to any disclaimer, the term of this patent is extended or adjusted under 35 U.S.C. 154(b) by 0 days.

(21) Appl. No.: 18/974,220

(22) Filed: Dec. 9, 2024

(65) Prior Publication Data

US 2025/0185911 A1     Jun. 12, 2025

Related U.S. Application Data

(60) Provisional application No. 63/607,437, filed on Dec. 7, 2023.

(51) Int. Cl.
| | |
|---|---|
| *A61B 8/00* | (2006.01) |
| *A61B 3/12* | (2006.01) |
| *A61B 5/00* | (2006.01) |
| *A61B 5/145* | (2006.01) |
| *A61B 5/1455* | (2006.01) |
| *G16H 10/60* | (2018.01) |

(52) U.S. Cl.
CPC ............ *A61B 3/12* (2013.01); *A61B 5/14546* (2013.01); *A61B 5/1455* (2013.01); *A61B 5/7203* (2013.01); *G16H 10/60* (2018.01)

(58) Field of Classification Search
CPC ....... A61B 3/12; A61B 5/1455; A61B 5/7203; A61B 5/14546
See application file for complete search history.

(56) References Cited

U.S. PATENT DOCUMENTS

| | | |
|---|---|---|
| 10,052,019 B1 | 8/2018 | Jiao et al. |
| 2006/0134004 A1* | 6/2006 | Gellermann ......... A61B 5/0059 |
| | | 600/315 |
| 2006/0244913 A1 | 11/2006 | Gellermann et al. |
| 2012/0327368 A1 | 12/2012 | Williams et al. |

(Continued)

OTHER PUBLICATIONS

Beatty, S., et al., "Macular pigment and age related macular degeneration", Brtish Journal of Ophthalmology, 1999; 83, pp. 867-877 (11 pages).

(Continued)

*Primary Examiner* — Joel F Brutus
(74) *Attorney, Agent, or Firm* — Michael Pack

(57) ABSTRACT

A system and method are provided for bimodal detection and/or imaging of macular pigments. Fundus autofluorescence spectroscopy is applied in a first and a second region of an eye to measure fluorescence values from the fluorescing pigment (e.g., lipofuscin). The first region can be a macula, which has a higher density of macular pigments, and the second region can be in the peripheral retina, which has a lower density of macular pigments. Fundus reflection spectroscopy is applied in the first and a second region of an eye, as a baseline image, to determine absorptions due to other pigments (e.g., melanin) than the macular pigments and the fluorescing pigment. The density of macular pigments is determined using the measures fluorescence values and the absorptions due to other pigments.

22 Claims, 6 Drawing Sheets

— 300

| |
|---|
| Use fundus autofluorescence (FAF) spectroscopy at a first wavelength to measure autofluorescence across a retina of an eye including, e.g., the macula and the peripheral retina) 302 |

↓

| |
|---|
| Use fundus reflection (FR) spectroscopy at a second wavelength to measure absorption due to other pigments across a retina of an eye including, e.g., the macula and the peripheral retina 304 |

↓

| |
|---|
| Determine the amount of the macular pigment (e.g., macular pigment optical density (MPOD) or a macular pigment optical volume (MPOV) in the retina by calculating the optical densities for the FAF and FR spectroscopic measurements, 306 |

↓

| |
|---|
| Apply corrections for cataract-induced opacity (if needed) 308 |

↓

| |
|---|
| Generate an image of the amount of the macular pigment in the retina and use the image to determine a treatment and track progress of a patient 310 |

(56) References Cited

U.S. PATENT DOCUMENTS

2015/0238075 A1* 8/2015 Sharifzadeh ............. A61B 3/14
351/246
2022/0351373 A1* 11/2022 Lad ........................ G16H 50/20

OTHER PUBLICATIONS

Berendschot, Tos T.J.M. and Dirk van Norren, "Objective determination of the macular pigment optical density using fundus reflectance spectroscopy", Archives of Biochemistry and Biophysics, ScienceDirect, Elsevier, vol. 430, 2004, pp. 149-155 (7 pages).

Bone, Richard A., et al., "Macular pigment, photopigments, and melanin: Distributions in young subjects determined by four-wavelength reflectometry", Vision Research, ScienceDirect, Elsevier, vol. 47, 2007, pp. 3259-3268 (10 pages).

Cideciyan, Artur V., et al., "Autofluorescence Imaging With Near-Infrared Excitation: Normalization by Reflectance to Reduce Signal From Choroidal Fluorophores", Retina, Investigative Ophthalmology Visual Science, vol. 56, 2015, pp. 3393-3406 (14 pages).

Delori, Francois C., "Autofluorescence method to measure macular pigment optical densities fluorometry and autofluorescence imaging", Archives of Biochemistry and Biophysics, ScienceDirect, Elsevier, vol. 430, 2004, pp. 156-162 (7 pages).

Delori, Francois C., "Spectrophotometer for noninvasive measurement of intrinsic fluorescence and reflectance of the ocular fundus", Applied Optics, vol. 33, No. 31, Nov. 1, 1994, pp. 7439-7452 (14 pages).

Delori, Francois C., et al., "Bimodal spatial distribution of macular pigment: evidence of a gender relationship", Journal of the Optical Society of America A, vol. 23, No. 3, Mar. 2006, pp. 521-538 (18 pages).

Delori, Francois C., et al., "Macular pigment density measured by autofluorescence spectrometry: comparison with reflectometry and heterochromatic flicker photometry", Journal of the Optical Society of America A, vol. 18, No. 6, Jun. 2001, pp. 1212-1230 (19 pages).

Schmitz-Valckenberg, Steffen, et al., "Fundus Autofluorescence and Progression of Age-related Macular Degeneration", Diagnostics and Surgical Techniques, Survey of Ophthalmology, vol. 54, No. 1, Jan.-Feb. 2009, pp. 96-116 (22 pages).

Sharifzadeh, Mohsen, et al., "Nonmydriatic fluorescence-based quantitative imaging of human macular pigment distributions", Journal of the Optical Society of America A, vol. 23, No. 10, Oct. 2006, pp. 2373-2387 (15 pages).

Mainster, Martin A., and Radwan Ajlan, "Clinical Photic Retinopathy: Mechanisms, Manifestations, and Misperceptions", Eds. D.M. Albert et al., Albert and Jakobiec's Principles and Practice of Ophthalmology, Springer Nature Switzerland AG, 2022, DOI https://doi.org/10.1007/978-3-030-42634-7_121, pp. 3777-3806 (30 pages).

* cited by examiner

Use fundus autofluorescence (FAF) spectroscopy at a first wavelength to measure autofluorescence across a retina of an eye including, e.g., the macula and the peripheral retina) 302

Use fundus reflection (FR) spectroscopy at a second wavelength to measure absorption due to other pigments across a retina of an eye including, e.g., the macula and the peripheral retina 304

Determine the amount of the macular pigment (e.g., macular pigment optical density (MPOD) or a macular pigment optical volume (MPOV)) in the retina by calculating the optical densities for the FAF and FR spectroscopic measurements, 306

Apply corrections for cataract-induced opacity (if needed) 308

Generate an image of the amount of the macular pigment in the retina and use the image to determine a treatment and track progress of a patient 310

FIG. 3

BIMODAL METHOD FOR DETECTION AND MEASUREMENT OF MACULAR PIGMENTS IN RETINA TISSUE

CROSS-REFERENCE TO RELATED APPLICATIONS

This application priority to U.S. provisional application No. 63/607,437, titled "BIMODAL METHOD FOR DETECTION AND MEASUREMENT OF MACULAR PIGMENTS IN RETINA TISSUE," and filed on Dec. 7, 2023, which is expressly incorporated by reference herein in its entirety.

BACKGROUND

Carotenoids, a family of organic pigments, are integral to the body's natural antioxidant defense mechanism. A plethora of epidemiological and experimental studies have underscored the protective role of these pigments, highlighting their potential to mitigate the risks of several health issues. An increased dietary intake of carotenoids has been associated with a decreased likelihood of a variety of conditions, including but not limited to, certain types of cancer, age-related macular degeneration (AMD), retinal aging, and other disorders precipitated by oxidative cell damage.

A substantial body of research has affirmed that carotenoids, especially those located in the macula, have considerable implications for ocular health. The macula is densely populated with lutein, zeaxanthin, and meso-zeaxanthin-carotenoids collectively known as macular pigment. These pigments are thought to confer a protective effect on the macula by filtering harmful blue light and quenching reactive oxygen species, thereby limiting the potential for oxidative stress and damage.

Therefore, the noninvasive measurement of macular carotenoid levels has garnered significant interest in the scientific community. It is hypothesized that lower levels of these pigments may correlate with an elevated risk of age-related macular degeneration (AMD), a leading cause of severe vision loss in older adults. By facilitating the reliable detection and measurement of these pivotal antioxidants, the present invention provides a powerful tool in the broader efforts to comprehend and combat retinal pathologies.

Techniques for measuring macular pigment optical density (MPOD) generally fall into one of two categories: subjective techniques and objective techniques.

One subjective technique is the psychophysical heterochromatic flicker photometry (HFP) test. This noninvasive approach hinges on the principle of color intensity matching of two separate light beams—one targeted at the fovea, the center of the retina, and the other aimed at the surrounding perifoveal area.

The HFP test can be used to estimate human macular pigment levels subjectively. The technique exploits the ability of a macular pigment to absorb blue light, which forms the basis for the comparative analysis between the foveal and perifoveal responses to alternately flickering blue and green light stimuli.

The HFP test has significant limitations, which are largely due to it being a psychophysical test that relies on the subject's response to visual stimuli, and thus can be influenced by individual differences in cognitive interpretation and attention. Furthermore, this method assumes that the subject's perifoveal region is devoid of macular pigment, an assumption that may not always hold true, thereby potentially leading to inaccurate estimates of MPOD.

Fundus autofluorescence (FAF) is a non-invasive imaging technique that can be used to map natural and pathological fluorophores in the posterior pole. For example, this technique can be applied for in vivo fundus imaging to characterize the intrinsic autofluorescent properties of the human retina using a fundus spectrophotometer. Technological advancements have led to the development of several commercially available FAF devices with respective strengths and weaknesses depending on the type of imaging used, the excitation wavelength employed, and the desired field of view. A survey of some of the techniques used for spectroscopic imaging of the eye including, e.g., autofluorescence of lipofuscin and reflectometry can be found in Delori et al., "Macular pigment density measured by autofluorescence spectrometry: comparison with reflectometry and heterochromatic flicker photometry," J. Opt. Soc. Am. A/Vol. 18, No. 6, p. 1212 (June 2001).

Improved techniques are desired to address the weaknesses in prior spectroscopic techniques for fundus imaging.

BRIEF SUMMARY

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure.

In some aspects, the techniques described herein relate to a method of measuring macular pigments in an eye, the method including: using a first spectroscopic technique at a first wavelength to measure a first fluorescence value from a fluorescing pigment in a first region of the eye and measure a second fluorescence value from the fluorescing pigment in a second region of the eye, the first region of the eye including a greater density of one or more macular pigments than the second region of the eye; using a second spectroscopic technique at a second wavelength to measure absorptions in the first region of the eye and the second region of the eye due to other pigments than the fluorescing pigment and the one or more macular pigments; and determining an amount of the one or more macular pigments in the first region of the eye using the first fluorescence value, the second fluorescence value, and the absorption values.

In some aspects, the techniques described herein relate to a computing apparatus including: one or more processors; and a memory storing instructions that, when executed by the one or more processors, configure the computing apparatus to: use a first spectroscopic technique at a first wavelength to measure a first fluorescence value from a fluorescing pigment in a first region of an eye and measure a second fluorescence value from the fluorescing pigment in a second region of the eye, the first region of the eye include a greater density of one or more macular pigments than the second region of the eye; use a second spectroscopic technique at a second wavelength to measure absorptions in the first region of the eye and the second region of the eye due to other pigments than the fluorescing pigment and the one or more macular pigments; and determine an amount of the one or more macular pigments in the first region of the eye using the first fluorescence value, the second fluorescence value, and the absorption values.

In some aspects, the techniques described herein relate to a non-transitory computer-readable storage medium, the computer-readable storage medium including instructions that when executed by a computer, cause the computer to: using a first spectroscopic technique at a first wavelength to measure a first fluorescence value from a fluorescing pigment in a first region of an eye and measure a second fluorescence value from the fluorescing pigment in a second region of the eye, the first region of the eye include a greater density of one or more macular pigments than the second region of the eye; using a second spectroscopic technique at a second wavelength to measure absorptions in the first region of the eye and the second region of the eye due to other pigments than the fluorescing pigment and the one or more macular pigments; and determine an amount of the one or more macular pigments in the first region of the eye using the first fluorescence value, the second fluorescence value, and the absorption values.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

FIG. 3 illustrates a flow diagram of a method for bimodal spectroscopic imaging in accordance with some embodiments.

DETAILED DESCRIPTION

Figure 1:
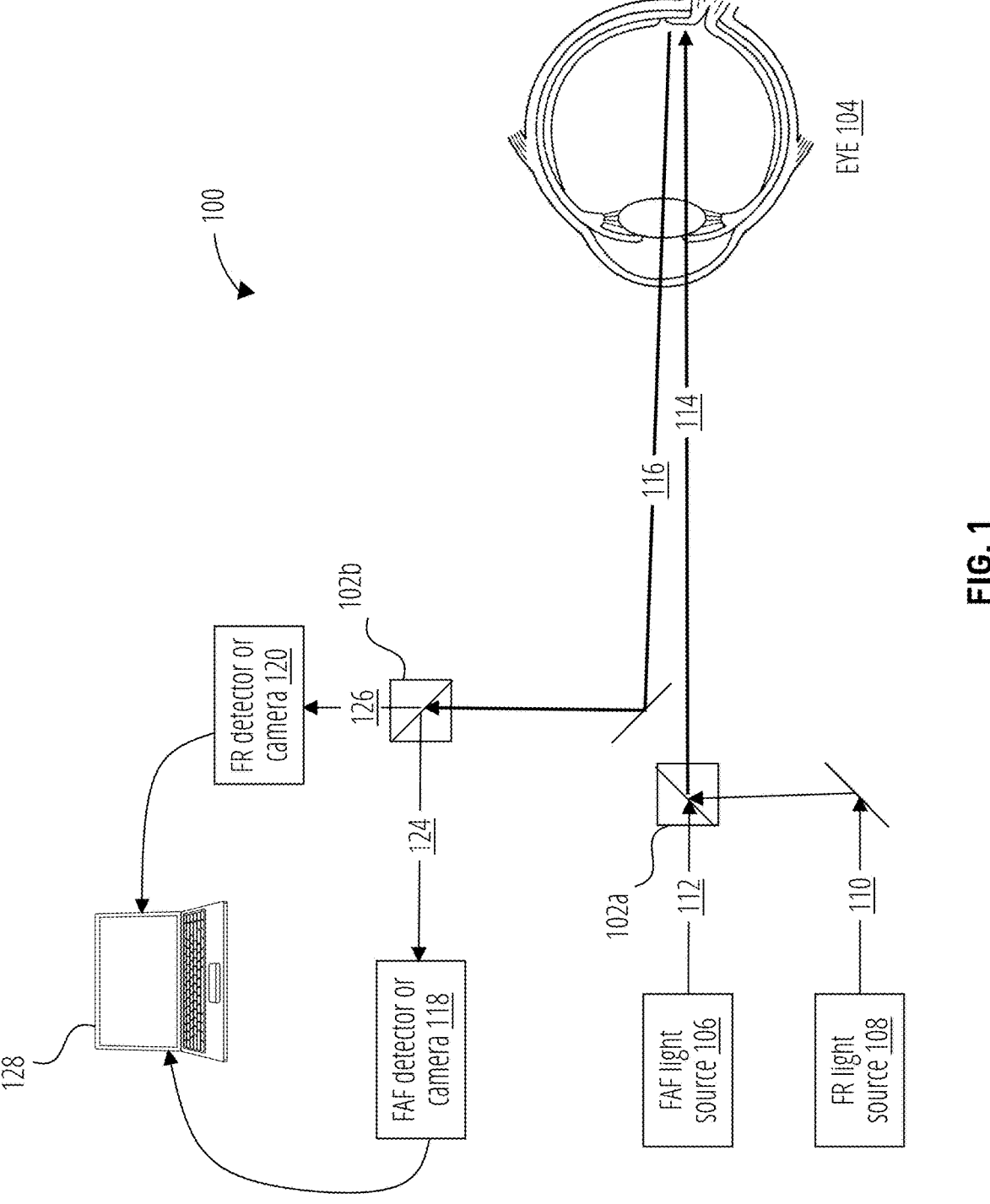
FIG. 1 illustrates a block diagram of a bimodal spectroscopic imaging system in accordance with some embodiments.

Macular pigment (MP) is a blue-absorbing pigment that is especially dense in the axons of the cone photoreceptors at the center of the macula (e.g., the area of the fovea of the center of the retina, see figure reproduced below). Interest in the macular pigment is largely based on its clinical relevance to age-related macular degeneration, which is an ocular disease that affects vision in older people. Various spectroscopy techniques can be used to measure MP levels, including, e.g., autofluorescence of lipofuscin and reflectometry. Used separately, autofluorescence and reflectometry can be fickle and inaccurate. It was an insight of the inventors that, when properly combined in a bimodal technique, a combination of Fundus Autofluorescence (FAF) spectroscopy together with Fundus Reflection (FR) spectroscopy can provide unexpected improvements in accuracy and robustness. For example, results for FAF spectroscopy based on lipofuscin fluorescence are susceptible to errors arising from the presence of other pigments than macular pigments and lipofuscin. Examples of other pigments can include melanin and/or hemoglobin.

Previously, FR spectroscopy and FAF spectroscopy have been performed independently, rather than being combined into a single measurement technique. For example, autofluorescence measurements of macular pigments that used lipofuscin fluorescence were previously performed using autofluorescence measurements as the baseline for normalization and/or calibration, whereas reflectometry measurements of macular pigments have been normalized and/or calibrated using other reflectometry measurements. The insight behind the bimodal methods and systems disclosed herein is that improved results with lower noise can be obtained by using reflectometry measurements to normalize autofluorescence measurements. This insight is unexpected and counterintuitive because the differences between these types of measurements suggest that they would not be compatible.

The systems and methods of bimodal imaging disclosed herein have several advantages over traditional methods such as fundus autofluorescence, enhancing the assessment and understanding of macular pigment distribution and concentration in the retina.

First, by leveraging two distinct wavelengths to excite lipofuscin and illuminate the retina, the bimodal approach can circumnavigate some of the inherent limitations presented in single-wavelength methodologies. This dual-excitation allows for more comprehensive and accurate mapping of macular pigments, reflecting their distribution and concentration more precisely than what can be achieved by single-wavelength techniques.

Second, the bimodal technique enables simultaneous measurements of autofluorescence and reflected light intensities at the macular and peripheral regions to provide enhanced reliability. For example, enhanced reliability can be provided by the integral accommodation for melanin absorption, which can potentially interfere with traditional methodologies. The bimodal approach effectively subtracts this absorption, mitigating its impact and ensuring a more precise calculation of macular pigment optical density (MPOD) and macular pigment optical volume (MPOV).

Third, the systems and methods disclosed herein can be used to generate a two-dimensional image of the MPOD, and this context for quantifying the distribution of macular pigment adds an additional layer of precision. It facilitates a comprehensive visualization and understanding of the spatial distribution of macular pigments, which is a significant advancement over traditional methods.

In summary, the bimodal imaging method represents a significant leap forward in the field of retinal imaging. By employing a dual-wavelength approach, it enhances precision, increases reliability, and offers a more comprehensive picture of the macular pigment distribution, making it a superior choice compared to traditional fundus autofluorescence methodologies.

FIG. 1 illustrates a non-limiting example of spectroscopy system. System 100 includes a light source for fundus autofluorescence (FAF) spectroscopy (i.e., FAF light source 106) emitting 1st wavelength light 112 and a light source for fundus reflection (FR) spectroscopy (i.e., FR light source 108) emitting 2nd wavelength light 110. Beam splitter 102*a* combines 1st wavelength light 112 and 2nd wavelength light 110 to provide combined beams 114, which is directed to a retina of eye 104. Return signals 116 includes reflectance for 2nd wavelength light 110 and fluorescence generated from 1st wavelength light 112. Beam splitter 102*b* separates fluorescence 124 from reflectance 126. Fluorescence 124 is detected by FAF detector or camera 118, and reflectance 126 is detected by FR detector or camera 120. The signals from FAF detector or camera 118 and FR detector or camera 120 are sent to processor 128, which processes them to generate a value or an image representing the amount of macular pigment in the macula of 104.

Bimodal imaging can be performed using system 100. Bimodal imaging advantageously provides non-invasive detection and quantification of macular pigments, including carotenoids, and other relevant substances present in the retinal tissue. The bimodal imaging method employs a dual imaging modality: fundus autofluorescence (FAF) and reflection imaging, operating synergistically to ensure an accurate and reliable measurement of Macular Pigment Optical Density (MPOD).

FAF can be used as an indicator of MPOD presence within the macular region. Lipofuscin autofluorescence spectroscopy, a core component of FAF, is used to estimate macular pigment levels. In this process, lipofuscin emission is excited at two distinct wavelengths: one coinciding with the absorption ranges of both macular pigment and lipofuscin, and another outside the absorption domain of macular pigment yet capable of stimulating lipofuscin emission.

This method allows for the calculation of macular pigment absorption through the logarithmic comparison of lipofuscin emission intensities in the peripheral retina and the macular area at both excitation wavelengths. This aspect of the process can be used for determining the precise absorption characteristics of the macular pigment.

Figure 2A:
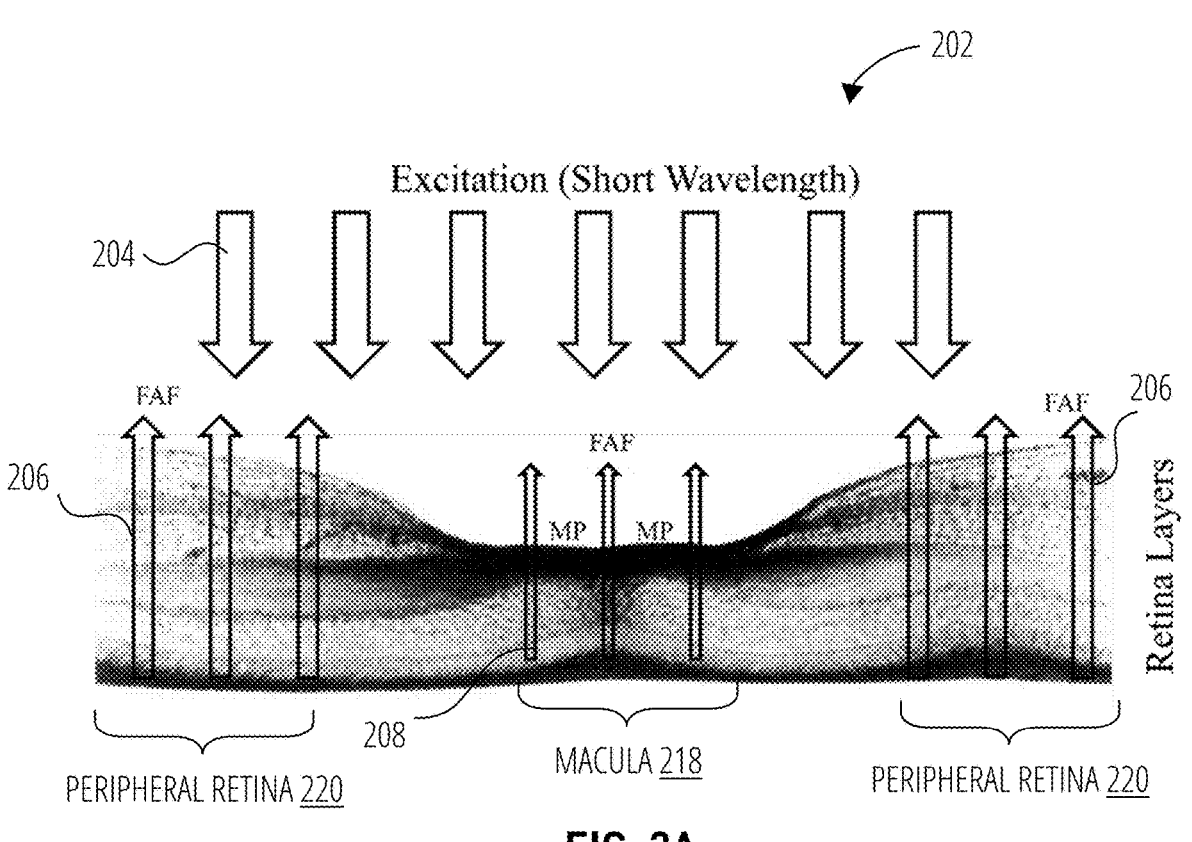
FIG. 2A illustrates an example of fundus autofluorescence spectroscopy in accordance with some embodiments.

FIG. 2A illustrates fundus autofluorescence spectroscopy 202. Irradiating light 204 (e.g., 1st wavelength light 112 from FAF light source 106) is directed to the retina layers. Peripheral-retina FAF 206 is the fluorescence generated in peripheral retina 220. Macula FAF 208 is the fluorescence generated in macula 218. When macular pigments are less concentrated in peripheral retina 220 than in macula 218, irradiating light 204 is less attenuated by the retina layers in peripheral retina 220, resulting in a higher intensity fluorescence signal in peripheral retina 220 than in macula 218. Thus, the fluorescence signal can be used to determine the concentration of macular pigments within the retina.

According to certain non-limiting examples, FIG. 2A illustrates a fundus autofluorescence (FAF) component of the bimodal method. Short-wavelength excitation light (e.g., 490 nm) gets attenuated by macular pigment, thereby inducing lipofuscin fluorescence. The resultant image, characterized by these unique interactions, is referred to as the FAF image.

Figure 2B:
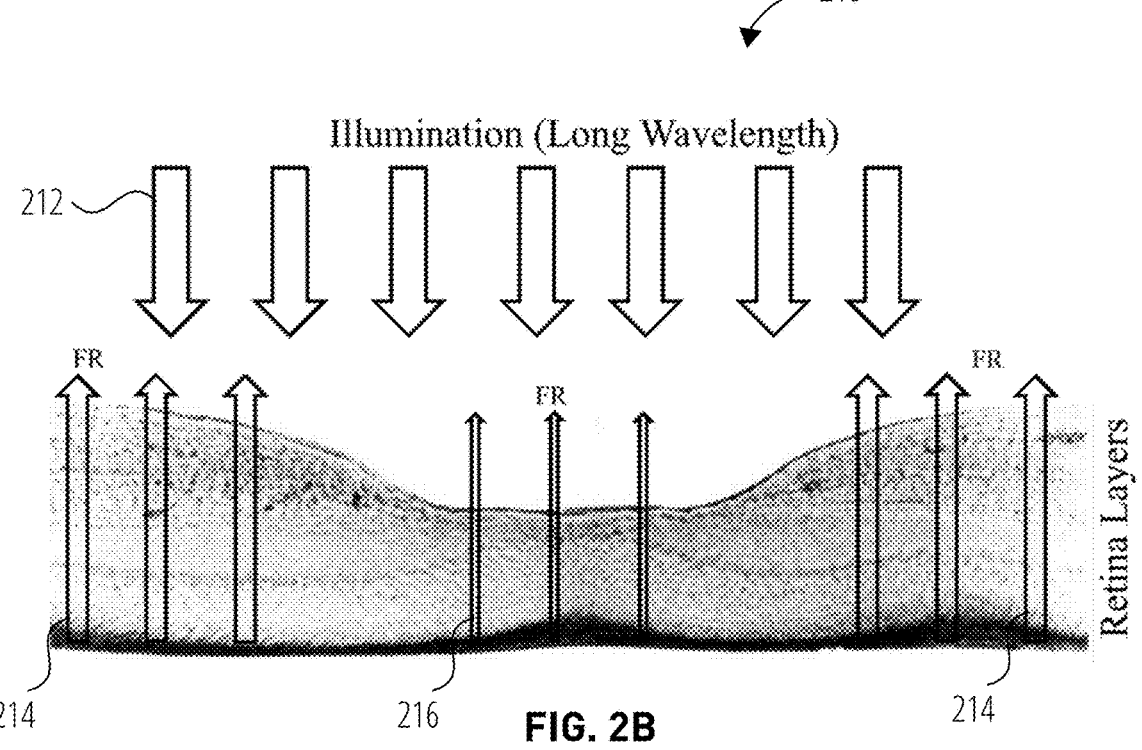
FIG. 2B illustrates an example of fundus reflection spectroscopy in accordance with some embodiments.

FIG. 2B illustrates fundus reflection spectroscopy 2102. Irradiating light 212 (e.g., 2nd wavelength light 110 from FR light source 108) is directed to the retina layers. Irradiating light 212 has a wavelength that is selected to be outside the absorption bands of the macular pigment(s) and lipofuscin but within the the absorption band of other pigment such as melanin. Thus, the amount of intensity of the reflectance (i.e., peripheral-retina reflection 214 and macula reflection 216) depends on the attenuation due to the other pigments, as dictated, e.g., by Beers law. The intensity of the reflectance can be used to determine the absorption, which is related to the density of the other pigments. The absorption determined from fundus reflection spectroscopy 210 can be used to remove the affects of the other pigments for the concentration of macular pigments that was determined using fundus autofluorescence spectroscopy 202.

According to certain non-limiting examples, FIG. 2A illustrates a fundus reflection (FR) component of the bimodal method. Long-wavelength illumination light (e.g., 650 nm) isn't attenuated by macular pigment but may be affected by other pigments such as melanin and hemoglobin. As this illumination falls outside the absorption band of lipofuscin, it does not stimulate lipofuscin fluorescence. The resulting image, defined by these specific properties, is referred to as the FR image.

Thus, FAF spectroscopy complements reflection imaging, which serves as a second imaging modality for the bimodal approach to establish a robust baseline that can be used to obtain the most accurate MPOD measurement. This synergy of autofluorescence and reflection imaging offers improved accuracy in MPOD measurements compared to other techniques such as standalone reflection and fundus autofluorescence methods.

In summary, this bimodal imaging provides an improvement relative to other non-invasive techniques for assessing macular pigment levels, combining the strengths of fundus autofluorescence and reflection imaging.

The bimodal method disclosed herein employs two distinctive light sources of differing wavelengths. The choice of wavelengths for these light sources contributes to the precision of this technique. The first light source, or the primary excitation source, has a wavelength that lies within the absorption spectrums of both lipofuscin and macular pigment. This selection enables it to excite lipofuscin and be absorbed by macular pigment, thereby leading to the generation of autofluorescence light.

The second light source, emits light of a longer wavelength. For example, this wavelength is situated outside the optical absorption spectra of macular pigment and lipofuscin. The emitted light from this source is not absorbed by these two pigments, but it can be absorbed by other pigments such as melanin, which results in double-pass absorption. This process contributes to the generation of reflected light, an important component of the measurement method.

This dual light source approach enables collection and analyzing of the autofluorescence light emanating from two distinct regions of the retina—the macula ($I_{mac}$) and the peripheral area ($I_{per}$). These regions are characterized by the presence of lipofuscin.

With the deployment of the primary light source, the intensity of lipofuscin emission in the macular region of the retina tends to be lower compared to the peripheral retina. This phenomenon is due to the absorption of the primary excitation light by the macular pigment, resulting in reduced lipofuscin excitation and therefore, weaker autofluorescence in the macular region.

In contrast, when the secondary light source is employed, lipofuscin, not absorbing this light, remains unexcited and hence, does not contribute to autofluorescence. However, this light might be absorbed by other pigments in the retina, particularly melanin, resulting in reflection light.

In essence, bimodal imaging leverages two strategically selected light sources and capitalizes on the properties of autofluorescence and reflection light to provide a more precise and reliable measurement of macular pigment levels.

The bimodal technique measures lipofuscin autofluorescence intensity generated by the first excitation wavelength (e.g., 490 nm but not limited to) and the intensity of the reflected light produced by the second wavelength (e.g., 650 nm but not limited to), both at the macula and the peripheral area.

These measurements then inform the calculation of macular pigment levels in the macular tissue according to the following formula:

$$MPOD = \left[ K \cdot \log\left(I_{per}/I_{mac}\right)_{490} - 1/2\, a \cdot \left(\log(I_{per}/I_{mac})_{650}\right], \right.$$

7

8 wherein the ½ factor incorporated in the second part of the equation accounts for the double pass absorption characteristic of all pigments excluding macular pigment and lipofuscin (e,g, melanin) and "a" is the compensation factor for the difference between absorption coefficients of other chromophores than macular pigment in the long wavelength (ex. 650 nm) and the wavelength that macular pigment absorption is maximum (ex. 460 nm) or at the location that macular pigment optical density is measured (ex. 490 nm).

As an example, if melanin is considered as the major chromophore in macula other than macular pigment, the factor "a" is the difference between the melanin absorption coefficient or extinction coefficient in 650 nm and 460 nm.

Upon establishing these intensity values, the distributions of macular pigment for the two excitation wavelengths can be quantified in a two-dimensional context as follows: MPOD=OD (FAF)–OD (FR), or more precisely:

$$MPOD = \left[ K \cdot \mathrm{Log} \left( I_{per}/I_{mac} \right)_{490\,nm} - 1/2\, a \cdot \left( \log \left( I_{per}/I_{mac} \right)_{650\,nm} \right]_{x,y} \right.$$

In this equation, 'x' and 'y' represent indices of the pixel array in the two-dimensional image. This added dimensionality grants this technique provides superior precision and a more comprehensive perspective of the macular pigment distribution in the retina.

Also in another version of the above equation, can be used to correct melanin in the place of 490 nm and then apply the correction factor on the whole equation:

$$MPOD = K \cdot \left[ \mathrm{Log} \left( I_{per}/I_{mac} \right)_{490\,nm} - 1/2\, b \cdot \left( \log \left( I_{per}/I_{mac} \right)_{650\,nm} \right]_{x,y} \right.$$

Here, b is the correction factor for the melanin absorption in the place 490 nm, and K is applied to the whole equation.

FIG. 3 illustrates an example method 300 for bimodal macular pigment detection and/or imaging. Although the example method 300 depicts a particular sequence of operations, the sequence may be altered without departing from the scope of the present disclosure. For example, some of the operations depicted may be performed in parallel or in a different sequence that does not materially affect the function of the method 300. In other examples, different components of an example device or system that implements the method 300 may perform functions at substantially the same time or in a specific sequence.

According to some examples, the method includes using fundus autofluorescence (FAF) spectroscopy at a first wavelength to measure autofluorescence across a retina of an eye including, e.g., the macula and the peripheral retina) at block 302. For example, FAF light source 106 and FAF detector or camera 118 illustrated in FIG. 1 may be used to perform fundus autofluorescence (FAF) spectroscopy at a first wavelength to measure autofluorescence across a retina of an eye including, e.g., the macula and the peripheral retina).

For example, the retina of the eye can be irradiated with light in the absorption bands of lipofuscin and the macular pigment(s) (e.g., in the wavelength range of about 400 nm to about 500 nm or in a wavelength range of about 480 nm to about 520 nm). The fluorescing pigment (e.g., lipofuscin) absorbs the first wavelength and emits fluorescent light at a longer wavelength. A detector or CCD camera can detect a two-dimensional image of the emitted fluorescence light at a longer wavelength than the first wavelength.

According to some examples, the method includes using fundus reflection (FR) spectroscopy at a second wavelength to measure absorption due to other pigments across a retina of an eye including, e.g., the macula and the peripheral retina at block 304. For example, FR light source 108 and FR detector or camera 120 illustrated in FIG. 1 may be used to perform fundus reflection (FR) spectroscopy at a second wavelength to measure absorption due to other pigments across a retina of an eye including, e.g., the macula and the peripheral retina.

For example, the retina of the eye can be irradiated with light outside the absorption bands of lipofuscin and the macular pigment(s) but within the absorption band of other pigments like melanin (e.g., the wavelength range of about 600 nm to about 900 nm). After passing through the retina layers where it is partially absorbed by the other pigments, the light reflects from the sclera and passes through the retina layers a second time before exiting the eye and being detected at a detector or CCD camera detects a two-dimensional image of the light that has been attenuated by twice passing through the retina layers. Because the second wavelength of light experiences only attenuation and elastic scattering, the light of reflectance return signal is at the second wavelength.

According to some examples, the method includes determining the amount of the macular pigment (e.g., macular pigment optical density (MPOD) or a macular pigment optical volume (MPOV)) in the retina by calculating the optical densities for the FAF and FR spectroscopic measurements, at block 306. For example, processor 128 illustrated in FIG. 1 may determine the amount of the macular pigment (e.g., macular pigment optical density (MPOD) or a macular pigment optical volume (MPOV)) in the retina by calculating the optical densities for the FAF and FR spectroscopic measurements.

According to some examples, the method includes applying corrections for cataract-induced opacity at block 308. For example, processor 128 illustrated in FIG. 1 may apply corrections for cataract-induced opacity.

According to some examples, the method includes generating an image of the amount of the macular pigment in the retina and use the image to determine a treatment and track progress of a patient at block 310. For example, processor 128 illustrated in FIG. 1 may generate an image of the amount of the macular pigment in the retina and use the image to determine a treatment and track progress of a patient.

Cataracts are a prevalent ocular condition characterized by the clouding of the crystalline lens within the eye, which can result in blurred vision and reduced contrast sensitivity. Typically associated with aging, but also potentially caused by trauma, medications, or congenital factors, cataracts interfere with the eye's ability to focus light effectively onto the retina. This disruption manifests as an overall reduction in image clarity, and in more severe cases, may lead to blindness if left untreated.

The onset of cataracts poses significant challenges to retinal imaging techniques. The primary complication arises from the scattering of light caused by the cloudy lens, which leads to a diffused, less focused image on the retinal plane. This scattering not only compromises image sharpness but also attenuates contrast, rendering it difficult to distinguish between various anatomical structures within the retina.

Furthermore, reduced contrast in retinal imaging can obfuscate details necessary for accurate diagnostic procedures. Specifically, the diminution of contrast impacts the delineation between different retinal layers and hinders the precise measurement of optical densities of various retinal constituents, such as macular pigments.

Macular pigment optical density (MPOD) can be used as a metric for assessing the health of the macula, a vital part of the retina responsible for central vision. Various optical techniques have been developed to measure MPOD with high precision, but the presence of cataracts introduces confounding variables that can compromise these measurements.

Cataracts can cause significant light scattering and absorption, leading to a lowered image contrast during retinal imaging. This is particularly problematic for the accurate quantification of MPOD. The diminished contrast often translates into an underestimated measurement of MPOD levels, which can lead clinicians to draw incorrect conclusions about the state of macular health. Given that macular pigment is important in filtering harmful blue light and plays a role in visual performance, an inaccurate reading can have far-reaching implications for patient care.

Given that cataracts lead to an underestimation of MPOD, it is beneficial to integrate a correction factor within the multimodal or bimodal imaging methods used for retinal assessments. This correction factor aims to adjust the MPOD readings, taking into account the light scattering and absorption caused by cataracts. By incorporating this compensatory measure, clinicians can achieve a more accurate MPOD estimation even in the presence of mild to moderate cataracts.

In summary, while cataracts pose challenges to retinal imaging and MPOD measurement, understanding these challenges enables the development of compensatory methods to ensure accurate assessments. As multimodal imaging technologies advance, incorporating such correction factors becomes increasingly feasible for the holistic understanding and treatment of ocular health.

Cataracts have long been a challenging factor in the accurate measurement of Macular Pigment Optical Density (MPOD) using imaging techniques. The scattering effects of cataracts can degrade image quality and contrast, thereby affecting the reliability of the measurements. This study presents a novel approach to compensate for these challenges by taking advantage of the specific optical properties of retinal veins and their absorption characteristics for hemoglobin, here as an example deoxyhemoglobin.

Methodology

The bimodal imaging technique employs two distinct images:

1—Fundus Autofluorescence (FAF), excited at a 490 nm wavelength, which leads to autofluorescence emission at wavelengths between 650-750 nm.

2—Fundus Reflection (FR), using a longer 650 nm wavelength as the baseline illumination.

Vein Optical Density as an Indicator of Cataract

Retinal veins, rich in deoxyhemoglobin, are beneficial for this assessment. We define A as the absorption coefficient ratio, where the absorption coefficient for deoxyhemoglobin at 490 nm is A times higher than at 650 nm. This allows for generalization beyond specific numerical values.

The optical density (OD) of the veins can be described by the following equations:

$$OD_{vein}(FAF) = OD_{vein}(490 \text{ nm}) + OD_{vein}(\lambda > 650 \text{ nm})$$

$$OD_{vein}(FR) = 2 \times OD_{vein}(650 \text{ nm})$$

$$OD_{vein}(490 \text{ nm}) = A \times OD_{vein}(650 \text{ nm})$$

Combining these equations, the expected OD of veins in the FAF should be A/2 times higher than that in the FR image:

$$OD_{vein}(FAF) = A/2 \times OD_{vein}(FR)$$

Correction Factor for Cataract Impact

The FR image, captured at wavelengths of 650 nm and above, is less impacted by cataract-induced scattering. Therefore, measuring the optical density of the veins in both FAF and FR images, and comparing it with the expected A/2 ratio, will indicate the presence of a cataract and allow the calculation of a correction factor for MPOD underestimation.

This method thus offers a significant improvement in the accuracy of MPOD measurements, especially in patients with non-severe cataracts.

Numerical Example for Cataract-Induced Image Degradation Compensation in Bimodal Imaging Parameters and Constants To offer a concrete example, we consider specific vein extinction coefficients for the respective wavelengths:

Vein extinction coefficient at 490 nm: $\varepsilon_{490nm}=16,684$

Vein extinction coefficient at 650-750 nm: $\varepsilon_{650\text{-}750nm}=2,001$ Vein extinction coefficient at 650 nm for the FR image: $\varepsilon_{650nm}^{FR}=3,750$.

Calculations for FAF Image

The vein extinction coefficient for the FAF image, which combines both the 490 nm excitation and 650-750 nm emission, can be calculated as:

$$\varepsilon_{FAF} = \varepsilon_{490} + \varepsilon_{650\text{-}750} = 16,684 + 2,001 = 18,685.$$

Calculations for FR Image

For the FR image, since the light undergoes a double pass through the vein, the effective vein extinction coefficient becomes:

$$\varepsilon_{FR} = 2 \times \varepsilon_{650nm}^{FR} = 2 \times 3,750 = 7,500.$$

Calculation of A for Cataract Indication

The ratio A serves as an indicator for cataract presence and its impact on the image. A can be calculated by comparing the vein extinction coefficients in the FAF and FR images:

$$A = \varepsilon_{FAF}/\varepsilon_{FR} = 18,685/7,500 \approx 2.49$$

The value of A can be used as an indicator for cataract presence and its degree of influence on image quality. It serves as a critical correction factor for calculating a more accurate Macular Pigment Optical Density (MPOD), particularly for patients with non-severe cataracts. By comparing the expected and measured values of A, one can identify the extent of cataract-induced degradation and implement a correction factor accordingly.

This numerical example illustrates how the method can be applied for the most accurate assessment of MPOD in clinical settings.

Applying Correction Factor to MPOD in the Presence of Cataract

In subjects with cataracts, the optical properties of the eye lens change, leading to a decrease in the image contrast of retinal images. This degradation affects the accuracy of measuring Macular Pigment Optical Density (MPOD) through the bimodal imaging methods. The attenuation due to cataracts acts as an unwanted noise, making it beneficial to correct for this factor for more accurate MPOD measurements.

To address this issue, we introduce a correction factor A, calculated based on the vein extinction coefficients in both the Autofluorescence Image (FAF) and Fundus Reflection (FR) images. This factor A is a quantitative measure of the cataract's impact on the imaging system's ability to accurately measure MPOD.

The corrected MPOD (MPOD corrected) can be calculated using the equation:

$$MPOD_{corrected} = MPOD_{measured} \times A,$$

wherein $MPOD_{measured}$ represents the MPOD value obtained from the FAF image without any correction. By multiplying this value by A, we obtain $MPOD_{corrected}$, which is an accurate measure of MPOD that accounts for the cataract-induced degradation in image quality.

Figure 4:
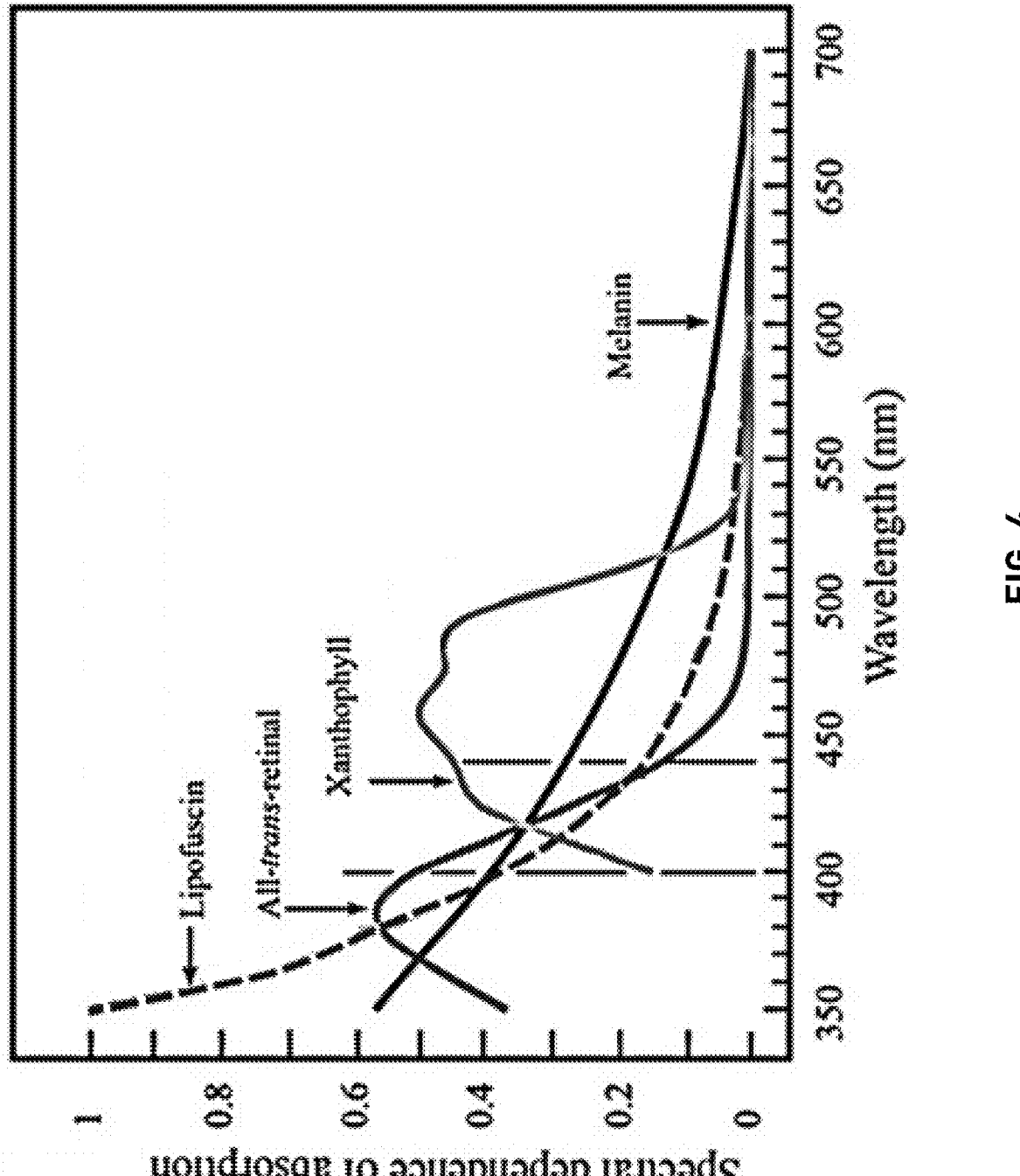
FIG. 4 illustrates a plot of absorption spectra of pigments in accordance with some embodiments.

FIG. 4 illustrates the optical absorption bands of macular pigment and lipofuscin, showing the overlapping absorption spectra of macular pigment and melanin. This overlap indicates that quantifying of melanin's optical density in the macula can improve the accuracy of measurements the macular pigment's optical density. This overlap indicates that accurate measurements will taken into account the complex interplay between these spectrally overlapping components.

Melanin, a natural pigment found in various tissues in the body, plays a critical role within the retina. Besides its widespread recognition as the pigment responsible for the coloration of skin, hair, and eyes, its complex structure and functional attributes make it indispensable for the retina's overall health and visual function.

In the retina, melanin is primarily found in the retinal pigment epithelium (RPE), the choroid, and the iris. Its multifaceted roles include protecting the eye from harmful UV radiation, absorbing scattered light, and contributing to various biochemical pathways for normal visual function.

The distribution of melanin in the retina is not uniform. It is more densely concentrated in the macula's central region, with the highest concentration located in the fovea. The fovea, a specialized region of the retina responsible for sharp, central vision, contains a remarkable amount of melanin that aids in the optimization of image quality.

This concentration in the macula and fovea is believed to be a defense mechanism against photooxidative damage, as these areas are exposed to a high degree of focused light. By absorbing excess light, melanin prevents potential damage to sensitive photoreceptors.

The retinal melanin coexists with other pigments such as the macular pigment, which contains carotenoids like lutein and zeaxanthin. These pigments are collectively responsible for absorbing and filtering short-wavelength light, further protecting the retinal tissues.

However, the overlapping absorption spectra of melanin and macular pigment, particularly in the blue region of the spectrum, create challenges in optical imaging. The two pigments work synergistically, but their similar absorption characteristics can lead to difficulties in distinguishing them in clinical measurements.

When assessing macular pigment optical density (MPOD), the presence of melanin requires careful consideration. Since melanin's optical density can overlap with that of the macular pigment, direct measurements can inadvertently incorporate melanin's characteristics, leading to inaccuracies.

Understanding the relationship between these two pigments and their combined effect on optical density is beneficial for accurate clinical evaluation and research.

The task of differentiating melanin's optical density from that of macular pigment is complex, requiring sophisticated methodologies. Various approaches, including spectral analysis, advanced imaging techniques, and computational algorithms, are employed to ensure accurate measurements.

The development of these techniques requires a multidisciplinary approach, combining the expertise of ophthalmologists, optical engineers, biophysicists, and other specialists.

The ability to accurately measure and differentiate the optical densities of melanin and macular pigment has far-reaching clinical implications. It can aid in the early detection of retinal diseases, enable more precise patient monitoring, and contribute to the development of novel therapeutic strategies.

Melanin's presence and unique distribution within the retina, particularly the macula and fovea, are of profound interest to researchers and clinicians alike. Its interplay with other pigments, such as the macular pigment, and its influence on visual function are complex subjects that demand ongoing exploration. The challenges associated with measuring melanin's optical density separately from that of other pigments underscore the benefits of continued improvements in imaging technology and analytical methods. By delving deeper into melanin's multifaceted role, we stand to gain critical insights that could revolutionize the way we approach visual health, disease detection, and treatment strategies.

Additionally, hemoglobin is an iron-rich protein responsible for transporting oxygen in the bloodstream, is present in the blood vessels of the retina. The concentration and distribution of hemoglobin within the retinal vasculature are nonuniform, with specific patterns observed in the macula and, most notably, in the fovea.

The fovea, as the central part of the macula, has a high density of photoreceptor cells and a complex vascular network to support its metabolic demands. The concentration of hemoglobin in this area can affect the optical properties of the retina, specifically the absorption characteristics.

Just as with melanin, the absorption spectrum of hemoglobin in the retina overlaps with the macular pigment's optical density. This overlap creates a complex scenario where the quantification of the macular pigment optical density requires careful separation from the optical density attributed to hemoglobin.

The nonuniform distribution of hemoglobin, along with its dynamic nature due to blood flow, presents unique challenges in isolating its optical density from that of macular pigment. This separation is crucial for accurate measurements and interpretations of the retinal images.

Innovative imaging techniques, such as multispectral imaging and optical coherence tomography angiography (OCTA), are being explored to differentiate the optical characteristics of hemoglobin from those of macular pigment. These methods provide detailed insights into the vascular structure and blood flow, aiding in the separation of the optical densities.

Understanding the presence and nonuniformity of hemoglobin in the retina is paramount in retinal imaging, especially in the context of quantifying macular pigment optical density. The interaction between hemoglobin, macular pigment, and other retinal components necessitates advanced methodologies and careful consideration in imaging protocols. By addressing the challenges related to hemoglobin's optical density, this understanding may pave the way for more precise and nuanced assessments of the retina, opening new avenues in retinal research and clinical practice. The novel method introduced in this patent, emphasizes the importance of accounting for hemoglobin in retinal imaging and provides supportive material to underscore the need for precise techniques to separate its optical density from macular pigment optical density. Integrating this understanding into the bimodal method can contribute to the overall effectiveness and reliability of retinal imaging techniques.

Figure 5A:
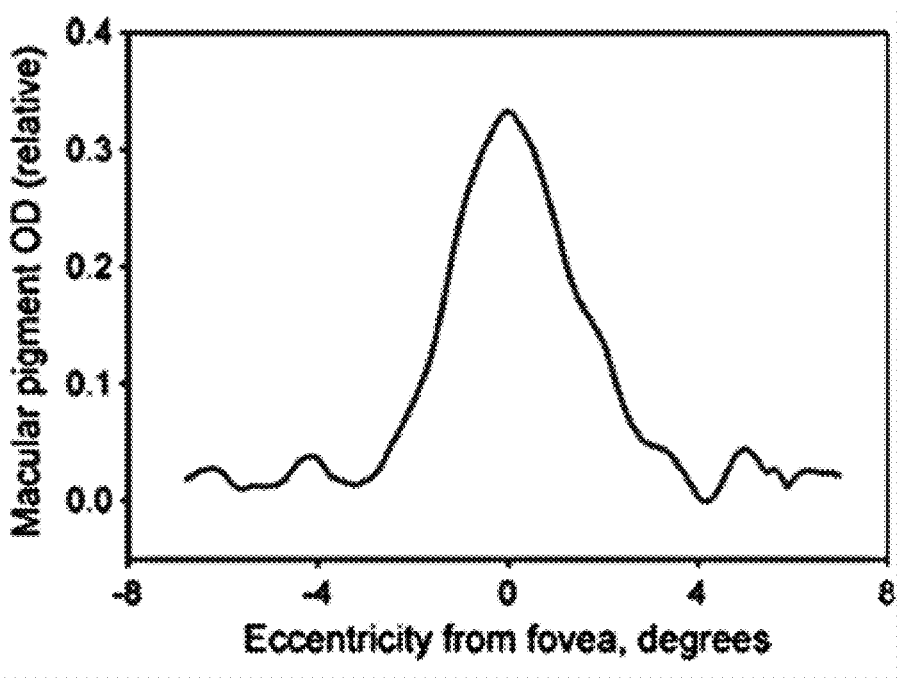
FIG. 5A illustrates a first lineout of macular pigment optical density in accordance with some embodiments.
Figure 5B:
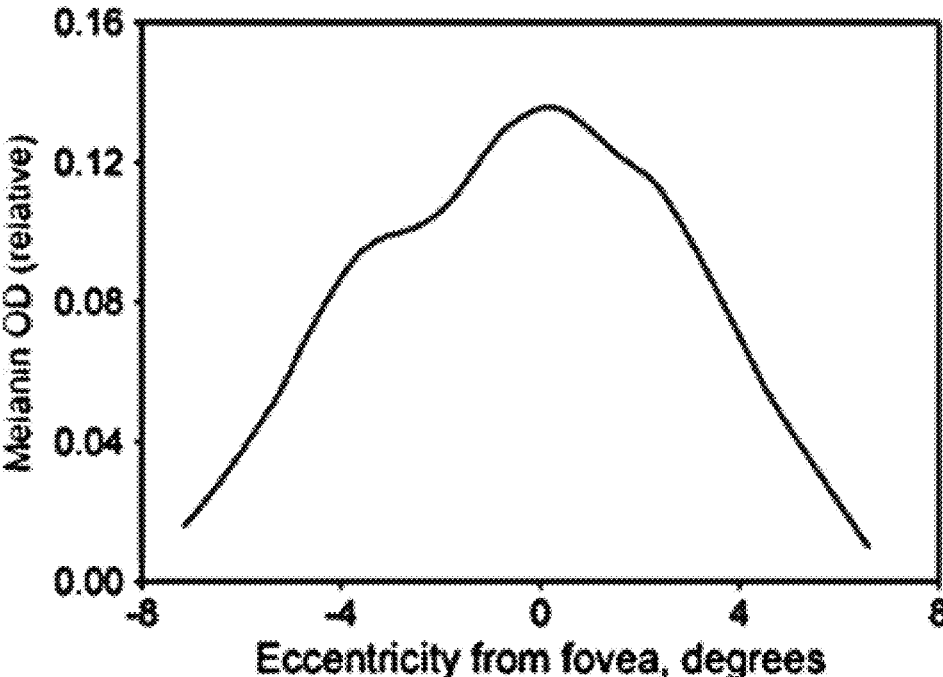
FIG. 5B illustrates as second lineout of melanin optical density in accordance with some embodiments.

FIGS. 5A and 5B illustrate horizontal line-scans through foveal regions. The displayed scans quantify the relative optical density distributions of the macular pigment (FIG. 5A), and melanin (FIG. 5B), both examined at 460 nm along a horizontal meridian crossing through the fovea. The light is scattered multiple times in the melanin layer or reflected at the sclera, returning through the varying layers. These plots reveal a concentrated presence of both macular pigment and melanin in the fovea. Notably, to accurately quantify the optical density of the macular pigment within the fovea, it becomes necessary to distinguish it from the optical density of melanin.

Figure 6:
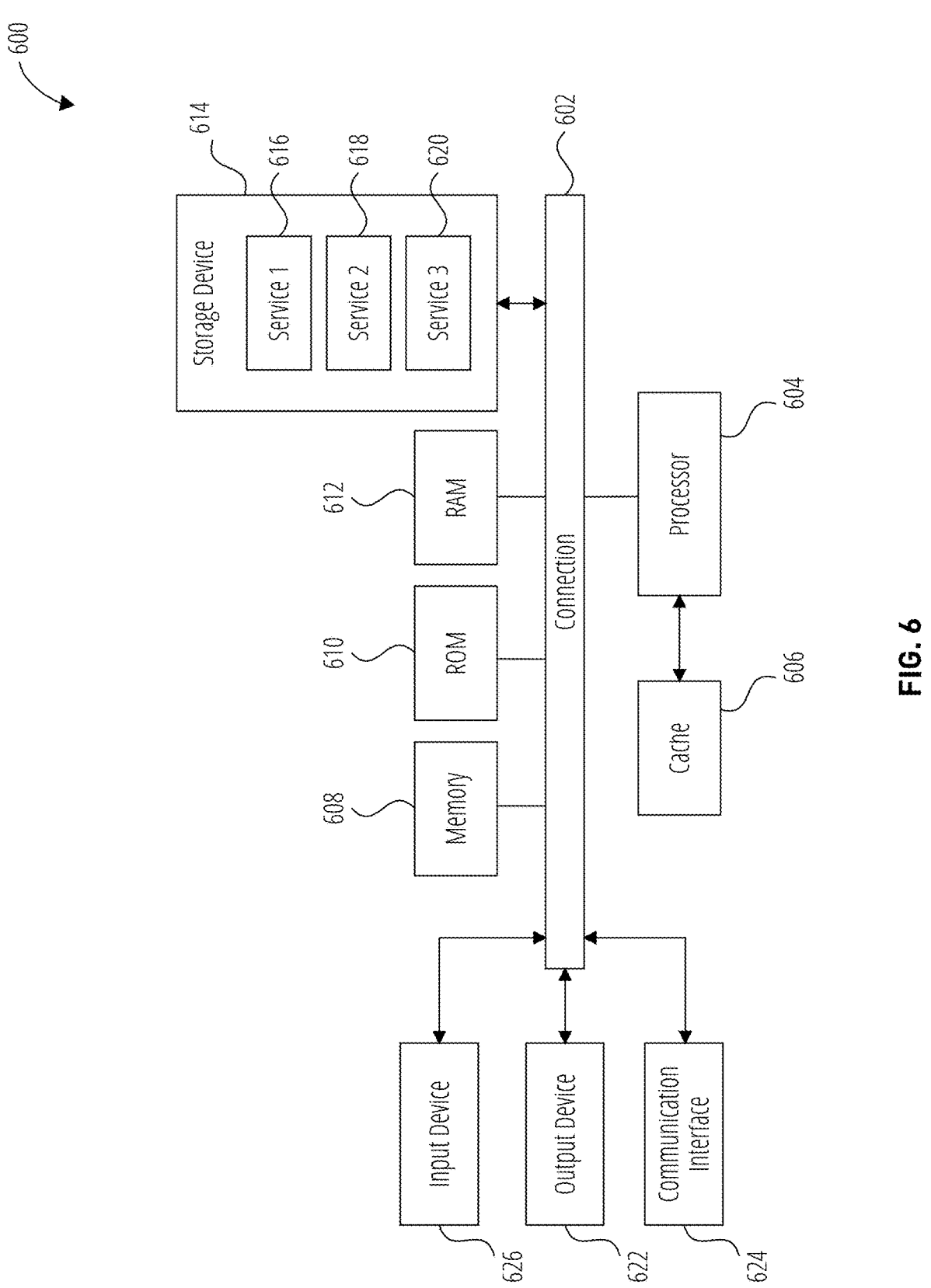
FIG. 6 shows an example of a computational system for implementing certain aspects of the present technology.

FIG. 6 shows an example of computing system 600, which can be for example any computing device making up processor 128 or any component thereof in which the components of the system are in communication with each other using connection 602. Connection 602 can be a physical connection via a bus, or a direct connection into processor 604, such as in a chipset architecture. Connection 602 can also be a virtual connection, networked connection, or logical connection.

In some embodiments, computing system 600 is a distributed system in which the functions described in this disclosure can be distributed within a datacenter, multiple data centers, a peer network, etc. In some embodiments, one or more of the described system components represents many such components each performing some or all of the function for which the component is described. In some embodiments, the components can be physical or virtual devices.

Example computing system 600 includes at least one processing unit (CPU or processor) 604 and connection 602 that couples various system components including system memory 608, such as read-only memory (ROM) 610 and random access memory (RAM) 612 to processor 604. Computing system 600 can include a cache of high-speed memory 606 connected directly with, in close proximity to, or integrated as part of processor 604.

Processor 604 can include any general purpose processor and a hardware service or software service, such as services 616, 618, and 620 stored in storage device 614, configured to control processor 604 as well as a special-purpose processor where software instructions are incorporated into the actual processor design. Processor 604 may essentially be a completely self-contained computing system, containing multiple cores or processors, a bus, memory controller, cache, etc. A multi-core processor may be symmetric or asymmetric.

To enable user interaction, computing system 600 includes an input device 626, which can represent any number of input mechanisms, such as a microphone for speech, a touch-sensitive screen for gesture or graphical input, keyboard, mouse, motion input, speech, etc. Computing system 600 can also include output device 622, which can be one or more of a number of output mechanisms known to those of skill in the art. In some instances, multimodal systems can enable a user to provide multiple types of input/output to communicate with computing system 600. Computing system 600 can include communication interface 624, which can generally govern and manage the user input and system output. There is no restriction on operating on any particular hardware arrangement, and therefore the basic features here may easily be substituted for improved hardware or firmware arrangements as they are developed.

Storage device 614 can be a non-volatile memory device and can be a hard disk or other types of computer readable media which can store data that are accessible by a computer, such as magnetic cassettes, flash memory cards, solid state memory devices, digital versatile disks, cartridges, random access memories (RAMs), read-only memory (ROM), and/or some combination of these devices.

The storage device 614 can include software services, servers, services, etc., that when the code that defines such software is executed by the processor 604, it causes the system to perform a function. In some embodiments, a hardware service that performs a particular function can include the software component stored in a computer-readable medium in connection with the necessary hardware components, such as processor 604, connection 602, output device 622, etc., to carry out the function.

Among the objective techniques for assessing macular pigment optical density (MPOD), reflection imaging stands out as a noninvasive and effective method. The foundational principle behind this approach involves the deployment of two distinct wavelengths of light.

The first wavelength is carefully selected to overlap with the optical absorption region of macular pigments, typically situated in the blue/green wavelengths region. The macular pigments—primarily lutein, zeaxanthin, and meso-zeaxanthin—are known to absorb short-wavelength light with peak absorption generally occurring around 460 nm, which lies in the blue portion of the visible light spectrum.

The second wavelength is chosen such that it either does not overlap or only partially overlaps with the optical absorption of the macular pigments. This often falls within the longer-wavelength, green-yellow region of the light spectrum. This light, not significantly absorbed by the macular pigments, acts as a reference, aiding in distinguishing the pigment's influence from other optical properties of the eye.

The methodology of reflection imaging leverages the differential absorption characteristics of these pigments to these two wavelengths. The measurements from these two wavelengths are then compared, and the resulting difference is used to calculate the MPOD. This is based on the principle that the level of reflected light decreases as the concentration of macular pigment increases, given its ability to absorb light in the blue/green spectrum.

This reflection imaging technique allows for a quantitative and spatial assessment of MPOD, offering an advantage over some subjective methods. However, it's worth noting that this approach can be influenced by factors such as lens and media opacities, macular abnormalities, and other pigments present in the retina. Thus, meticulous calibration and interpretation are crucial for accurate results.

Fundus autofluorescence (FAF) is a pioneering method employed for noninvasive measurement of macular pigment optical density (MPOD). This technique relies on the fluorescent properties of lipofuscin, a pigment contained in the retinal pigment epithelium (RPE), which is excited by light within specific wavelength ranges.

In the FAF method, lipofuscin is targeted with two distinct wavelengths: one within the optical absorption range of macular pigments (typically in the blue region) and another outside of this range but still within the optical absorption zone of lipofuscin (generally in the green region). This is due to the spectral characteristics of these pigments, where lipofuscin can absorb light across the blue and green wavelength regions, while macular pigment predominantly absorbs in the blue wavelength region and minimally or does not absorb light in the longer wavelengths, from green onward.

The principle underlying this technique is to estimate the absorption of macular pigment by measuring lipofuscin fluorescence intensity levels at two different retinal regions—the macula and peripheral retina, symbolized as $I_{mac}$ and $I_{per}$, respectively—at both excitation wavelengths. The resulting formula to calculate MPOD using FAF is expressed as:

$$MPOD = K * \left[\log\left(I_{per}/I_{mac}\right)_{blue} - \log\left(I_{per}/I_{mac}\right)_{green}\right]$$

Here, K represents the difference of the macular pigment (MP) extinction coefficient at the peak of the absorption band (~460 nm) and the position of the two excitation lights. For instance, in the case of two different excitation wavelengths in the blue and green regions, K approximates 1.2. However, it's crucial to note that the presence of other pigments in the retina which absorb short-wavelength excitation light (for instance, blue-green) necessitates the use of a second wavelength that is either not absorbed or minimally absorbed by macular pigment, but is absorbed by other pigments. This is essential for accurate estimation of macular pigment and forms the 'baseline' required for precise MPOD measurement.

FAF leverages the fluorescent properties of lipofuscin within the retinal pigment epithelium (RPE) to generate an image, eliminating the need for fluorescein dye injection. Lipofuscin, a byproduct of the lysosomal breakdown of photoreceptor outer segments, comprises several bis-retinoids, including A2E, A2PE, isoA2E, and A2-DHP-PE. These bisretinoids, when exposed to a light source, absorb blue light with a peak excitation wavelength of 470 nm and emit yellow-green light with a peak wavelength of 600 nm. An emission detector records these signals to create an image that serves as a lipofuscin density map, with brighter areas signifying regions of higher lipofuscin density. Given that many retinal pathologies often result in RPE dysfunction and lipofuscin accumulation, abnormal autofluorescence patterns on FAF imaging can act as markers for retinal disease.

In the context of our dual-modal method, fundus autofluorescence serves as the first imaging modality. Here, a particular wavelength designed to excite lipofuscin is used.

This wavelength is carefully chosen for its overlap with the optical absorption bands of both lipofuscin and macular pigment.

On the other hand, reflection imaging, the second mode, employs light of a wavelength that doesn't coincide with the optical absorption band of macular pigments. In this phase, the light traverses the macular pigment layer and is reflected off structures such as the sclera, while pigments like melanin, which have absorption bands overlapping with the excitation wavelengths, absorb this light.

Thus, this dual-modal approach provides a comprehensive strategy for measuring macular pigment levels. Fundus autofluorescence yields information on the macular pigment level, while reflection imaging provides a reliable baseline for obtaining the most accurate estimation of macular pigment optical density (MPOD). The integration of these two modalities not only enhances our understanding of macular pigment distribution but also broadens our scope for assessing retinal health.

For clarity of explanation, in some instances, the present technology may be presented as including individual functional blocks including functional blocks comprising devices, device components, steps or routines in a method embodied in software, or combinations of hardware and software.

Any of the steps, operations, functions, or processes described herein may be performed or implemented by a combination of hardware and software services or services, alone or in combination with other devices. In some embodiments, a service can be software that resides in memory of a client device and/or one or more servers of a content management system and perform one or more functions when a processor executes the software associated with the service. In some embodiments, a service is a program or a collection of programs that carry out a specific function. In some embodiments, a service can be considered a server. The memory can be a non-transitory computer-readable medium.

In some embodiments, the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer-readable media. Such instructions can comprise, For example, instructions and data which cause or otherwise configure a general purpose computer, special purpose computer, or special purpose processing device to perform a certain function or group of functions. Portions of computer resources used can be accessible over a network. The executable computer instructions may be, For example, binaries, intermediate format instructions such as assembly language, firmware, or source code. Examples of computer-readable media that may be used to store instructions, information used, and/or information created during methods according to described examples include magnetic or optical disks, solid-state memory devices, flash memory, USB devices provided with non-volatile memory, networked storage devices, and so on.

Devices implementing methods according to these disclosures can comprise hardware, firmware and/or software, and can take any of a variety of form factors. Typical examples of such form factors include servers, laptops, smartphones, small form factor personal computers, personal digital assistants, and so on. The functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures. Aspects:

The present technology includes computer-readable storage mediums for storing instructions, and systems for executing any one of the methods embodied in the instructions addressed in the aspects of the present technology presented below:

Aspect 1. A method of measuring macular pigments in an eye, the method comprising: using a first spectroscopic technique at a first wavelength to measure a first fluorescence value from a fluorescing pigment in a first region of the eye and measure a second fluorescence value from the fluorescing pigment in a second region of the eye, the first region of the eye including a greater density of one or more macular pigments than the second region of the eye; using a second spectroscopic technique at a second wavelength to measure absorptions in the first region of the eye and the second region of the eye due to other pigments than the fluorescing pigment and the one or more macular pigments; and determining an amount of the one or more macular pigments in the first region of the eye using the first fluorescence value, the second fluorescence value, and the absorption values.

Aspect 2. The method of aspect 1, wherein determining the amount of the one or more macular pigments includes using the measured absorptions to remove a value absorption due to the other pigments from a determination of macular-pigment absorption.

Aspect 3. The method of aspect 1, wherein: the first spectroscopic technique is fundus autofluorescence (AFA), the second spectroscopic technique is fundus reflection (FR) in which an intensity is measured for return light that is reflected by a sclera of the eye as a baseline image for macular pigments optical density measurement, the first region of the eye includes a foveal area or a part of a macula of the eye, the second region of the eye includes a perifoveal area or a part of a peripheral retina of the eye, the second spectroscopic technique is fundus reflection (FR) in which an intensity is measured for return light that is reflected by a sclera of the eye, amount of the one or more macular pigments is a macular pigment optical density (MPOD) or a macular pigment optical volume (MPOV), the fluorescing pigment is lipofuscin, the other pigments include at least one of melanin or hemoglobin, and the one or more macular pigments include at least one of a carotenoid, lutein, zeaxanthin, or meso-zeaxanthin.

Aspect 4. The method of aspect 3, wherein the first fluorescence value and the second fluorescence value are measured by filtering fluorescent light from the eye using a high-pass filter that attenuates wavelengths shorter than a fluorescence wavelength of the fluorescing pigment.

Aspect 5. The method of aspect 1, wherein: the first wavelength is within an absorption band of the fluorescing pigment and within an absorption band of the one or more macular pigments, and the first wavelength is within a wavelength range of about 480 nm to about 520 nm.

Aspect 6. The method of aspect 1, wherein: the second wavelength is outside of an absorption band of the fluorescing pigment and outside an absorption band of the one or more macular pigments, and the first wavelength is in a wavelength range of about 600 nm to about 900 nm.

Aspect 7. The method of aspect 1, wherein determining the amount of the one or more macular pigments further includes: calculating a difference between a first optical density and a second optical density, the first optical density including a logarithm of a ratio between the second fluorescence value and the first fluorescence, and the second optical density representing difference between the absorption values or the logarithm of a ratio between intensities for the absorption values.

Aspect 8. The method of aspect 7, wherein calculating the difference between the first optical density and the second optical density includes: calculating the first optical density, which is a fundus autofluorescence (FAF) optical density, according to:

$$OD_{FAF} = K \times Log \left(\frac{I_{per}}{I_{mac}}\right)_{\lambda_1},$$

wherein $OD_{FAF}$ is the FAF optical density, K is a to: predefined constant relating a first extinction coefficient at a peak wavelength of an absorption band and a second extinction coefficient at the first wavelength, $I_{Per}$ is an intensity or irradiance of fluorescent light from a peripheral retina of the eye, $I_{mac}$ is the intensity or irradiance of fluorescent light from a macula of the eye, and $\lambda_1$ is the first wavelength; and calculating the second optical density, which is a fundus reflection (FR) optical density, according to:

$$OD_{FR} = \frac{a}{2} \times Log \left(\frac{I_{per}}{I_{mac}}\right)_{\lambda_2},$$

wherein $OD_{FR}$ is the FR optical density, $\alpha$ is a predefined constant relating a first absorption coefficient of the other pigments at the second wavelength to a second absorption coefficient of the other pigments at the first wavelength, $I_{per}$ is the intensity or irradiance of reflected light at the second wavelength from a peripheral retina of the eye, $I_{mac}$ is the intensity or irradiance of reflected light at the second wavelength from a macula of the eye, and $\lambda_2$ is the second wavelength.

Aspect 9. The method of aspect 1, further comprising: generating, based on the amount of the one or more macular pigments, an image that represents a density of the one or more macular pigments with respect to position on a retina of the eye.

Aspect 10. The method of aspect 1, further comprising: determining a correction factor for cataracts; and applying the correction factor to the amount of the one or more macular pigments to provide a corrected amount of the one or more macular pigments.

Aspect 11. The method of aspect 10, wherein the correction factor is calculated based on vein extinction coefficients in a fundus autofluorescence (FAF) image and a fundus reflection (FR) image in accordance with $$A = \frac{\varepsilon_{FAF}}{\varepsilon_{FR}},$$

wherein A is the correction factor, $\varepsilon_{FAF}$ is an FAF extinction coefficient, and EFR is an FR extinction coefficient.

Aspect 12. The method of aspect 10, further comprising: using the amount of the one or more macular pigments to determine a treatment for treating a patient for age-related macular degeneration (AMD) or retinitis pigmentosa.

Aspect 13. The method of aspect 10, wherein determining the correction factor for the cataracts includes: measuring vein-extinction coefficients for both the first spectroscopic technique and the second spectroscopic technique; calculating the correction factor based on a ratio of a vein extinction coefficients between the first spectroscopic technique and the second spectroscopic technique, and applying the correction factor includes using the correction factor to adjust the amount of the one or more macular pigments, thereby compensating for cataract-related degradation.

Aspect 14. The method of aspect 1, further comprising: storing, in a medical database, the amount of the one or more macular pigments in association a patient; and analyzing the amount of the one or more macular pigments using a longitudinal tracking analysis to monitor cataract progression of the patient with respect to time.

Aspect 15. The method of aspect 1, further comprising: dynamically adjusting an intensity of a one or more light sources irradiating the eye for the first spectroscopic technique based on a retinal reflectance of the eye, the intensity being dynamically adjusted to optimize signal-to-noise ratios for the first fluorescence value and/or the second fluorescence value.

Aspect 16. The method of aspect 15, further comprising: dynamically adjusting the intensity of another light source irradiating the eye for the second spectroscopic technique based on a retinal reflectance of the eye, the intensity of the another light source being dynamically adjusted to optimize a signal-to-noise ratio for one or more of the measure absorptions.

Aspect 17. The method of aspect 1, further comprising: using the amount of the one or more macular pigments to determine raw macular pigment optical density (MPOD) values and corrected MPOD values; and causing a display to display a user interface for patient monitoring and management, the user interface being configured to display the raw MPOD value together with the corrected MPOD values alongside one or more graphical representations of a macular pigment distribution and one or more density changes with respect to time.

Aspect 18. A computing apparatus comprising: one or more processors; and a memory storing instructions that, when executed by the one or more processors, configure the computing apparatus to: use a first spectroscopic technique at a first wavelength to measure a first fluorescence value from a fluorescing pigment in a first region of an eye and measure a second fluorescence value from the fluorescing pigment in a second region of the eye, the first region of the eye include a greater density of one or more macular pigments than the second region of the eye; use a second spectroscopic technique at a second wavelength to measure absorptions in the first region of the eye and the second region of the eye due to other pigments than the fluorescing pigment and the one or more macular pigments; and determine an amount of the one or more macular pigments in the first region of the eye using the first fluorescence value, the second fluorescence value, and the absorption values.

Aspect 19. The computing apparatus of aspect 18, wherein the instructions cause the computing apparatus to determine the amount of the one or more macular pigments by configuring the computing apparatus to: wherein determining the amount of the one or more macular pigments includes using the measured absorptions to remove a value absorption due to the other pigments from a determination of macular-pigment absorption.

Aspect 20. The computing apparatus of aspect 18, wherein: the first spectroscopic technique is fundus auto-fluorescence (AFA), the second spectroscopic technique is fundus reflection (FR) in which an intensity is measured for return light that is reflected by a sclera of the eye as a baseline image for macular pigments optical density measurement, the first region of the eye includes a foveal area or a part of a macula of the eye, the second region of the eye includes a perifoveal area or a part of a peripheral retina of the eye, the second spectroscopic technique is fundus reflection (FR) in which an intensity is measured for return light that is reflected by a sclera of the eye, amount of the one or more macular pigments is a macular pigment optical density (MPOD) or a macular pigment optical volume (MPOV), the fluorescing pigment is lipofuscin, the other pigments include at least one of melanin or hemoglobin, and the one or more macular pigments include at least one of a carotenoid, lutein, zeaxanthin, or meso-zeaxanthin.

Aspect 21. The computing apparatus of aspect 20, wherein the first fluorescence value and the second fluorescence value are measured by filtering fluorescent light from the eye using a high-pass filter that attenuates wavelengths shorter than a fluorescence wavelength of the fluorescing pigment Aspect 22. The computing apparatus of aspect 18, wherein: the first wavelength is within an absorption band of the fluorescing pigment and within an absorption band of the one or more macular pigments, and the first wavelength is within a wavelength range of about 480 nm to about 520 nm.

Aspect 23. The computing apparatus of aspect 18, wherein: the second wavelength is outside of an absorption band of the fluorescing pigment and outside an absorption band of the one or more macular pigments, and the first wavelength is in a wavelength range of about 600 nm to about 900 nm.

Aspect 24. The computing apparatus of aspect 18, wherein the instructions cause the computing apparatus to determine the amount of the one or more macular pigments by configuring the computing apparatus to: calculate a difference between a first optical density and a second optical density, the first optical density including a logarithm of a ratio between the second fluorescence value and the first fluorescence, and the second optical density representing difference between the absorption values or the logarithm of a ratio between intensities for the absorption values.

Aspect 25. The computing apparatus of aspect 24, wherein the instructions cause the computing apparatus to calculate the difference between the first optical density and the second optical density by configuring the computing apparatus to: calculate the first optical density, which is a fundus autofluorescence (FAF) optical density, according to:

$$OD_{FAF} = K \times \mathrm{Log}\left(\frac{I_{per}}{I_{mac}}\right)_{\lambda_1},$$

wherein $OD_{FAF}$ is the FAF optical density, K is a predefined constant relating a first extinction coefficient at a peak wavelength of an absorption band and a second extinction coefficient at the first wavelength, $I_{per}$ is an intensity or irradiance of fluorescent light from a peripheral retina of the eye, $I_{mac}$ is the intensity or irradiance of fluorescent light from a macula of the eye, and $\lambda_1$ is the first wavelength; and calculate the second optical density, which is a fundus reflection (FR) optical density, according to:

$$OD_{FR} = \frac{a}{2} \times \text{Log} \left( \frac{I_{per}}{I_{mac}} \right)_{\lambda_2},$$

wherein $OD_{FR}$ is the FR optical density, a is a to:

predefined constant relating a first absorption coefficient of the other pigments at the second wavelength to a second absorption coefficient of the other pigments at the first wavelength, $I_{per}$ is the intensity or irradiance of reflected light at the second wavelength from a peripheral retina of the eye, $I_{mac}$ is the intensity or irradiance of reflected light at the second wavelength from a macula of the eye, and $\lambda_2$ is the second wavelength.

Aspect 26. The computing apparatus of aspect 18, wherein the instructions further configure the computing apparatus to: generate, based on the amount of the one or more macular pigments, an image that represents a density of the one or more macular pigments with respect to position on a retina of the eye.

Aspect 27. The computing apparatus of aspect 18, wherein the instructions further configure the computing apparatus to: determine a correction factor for cataracts; and apply the correction factor to the amount of the one or more macular pigments to provide a corrected amount of the one or more macular pigments.

Aspect 28. The computing apparatus of aspect 27, wherein the instructions cause the computing apparatus to determine the correction factor by configuring the computing apparatus to: determine the correction factor by calculating the correction factor based on vein extinction coefficients in a fundus autofluorescence (FAF) image and a fundus reflection (FR) image in accordance with $$A = \frac{\varepsilon_{FAF}}{\varepsilon_{FR}},$$

wherein A is the correction factor, $\varepsilon_{FAF}$ is an FAF extinction coefficient, and $FR is an FR extinction coefficient.

Aspect 29. The computing apparatus of aspect 27, wherein the instructions further configure the computing apparatus to: use the amount of the one or more macular pigments to determine a treatment for treating a patient for age-related macular degeneration (AMD) or retinitis pigmentosa.

Aspect 30. The computing apparatus of aspect 27, wherein the instructions cause the computing apparatus to determine the amount of the one or more macular pigments by configuring the computing apparatus to: measure vein-extinction coefficients for both the first spectroscopic technique and the second spectroscopic technique; calculate the correction factor based on a ratio of a vein extinction coefficients between the first spectroscopic technique and the second spectroscopic technique, and apply the correction factor includes using the correction factor to adjust the amount of the one or more macular pigments, thereby compensating for cataract-related degradation.

Aspect 31. The computing apparatus of aspect 18, wherein the instructions further configure the computing apparatus to: store, in a medical database, the amount of the one or more macular pigments in association a patient; and analyze the amount of the one or more macular pigments using a longitudinal tracking analysis to monitor cataract progression of the patient with respect to time.

Aspect 32. The computing apparatus of aspect 18, wherein the instructions further configure the computing apparatus to: dynamically adjust an intensity of a one or more light sources irradiating the eye for the first spectroscopic technique based on a retinal reflectance of the eye, the intensity being dynamically adjusted to optimize signal-to-noise ratios for the first fluorescence value and/or the second fluorescence value.

Aspect 33. The computing apparatus of aspect 32, wherein the instructions further configure the computing apparatus to: dynamically adjust the intensity of another light source irradiating the eye for the second spectroscopic technique based on a retinal reflectance of the eye, the intensity of the another light source being dynamically adjusted to optimize a signal-to-noise ratio for one or more of the measure absorptions.

Aspect 34. The computing apparatus of aspect 18, wherein the instructions further configure the computing apparatus to: use the amount of the one or more macular pigments to determine raw macular pigment optical density (MPOD) values and corrected MPOD values; and cause a display to display a user interface for patient monitoring and management, the user interface being configured to display the raw MPOD value together with the corrected MPOD values alongside one or more graphical representations of a macular pigment distribution and one or more density changes with respect to time.

Aspect 35. A non-transitory computer-readable storage medium, the computer-readable storage medium including instructions that when executed by a computer, cause the computer to: using a first spectroscopic technique at a first wavelength to measure a first fluorescence value from a fluorescing pigment in a first region of an eye and measure a second fluorescence value from the fluorescing pigment in a second region of the eye, the first region of the eye include a greater density of one or more macular pigments than the second region of the eye; using a second spectroscopic technique at a second wavelength to measure absorptions in the first region of the eye and the second region of the eye due to other pigments than the fluorescing pigment and the one or more macular pigments; and determine an amount of the one or more macular pigments in the first region of the eye using the first fluorescence value, the second fluorescence value, and the absorption values.

Aspect 36. The non-transitory computer-readable storage medium of aspect 35, wherein the instructions cause the computer to determine the amount of the one or more macular pigments by causing the computer to: wherein determining the amount of the one or more macular pigments includes using the measured absorptions to remove a value absorption due to the other pigments from a determination of macular-pigment absorption.

Aspect 37. The non-transitory computer-readable storage medium of aspect 35, wherein: the first spectroscopic technique is fundus autofluorescence (AFA), the second spectroscopic technique is fundus reflection (FR) in which an intensity is measured for return light that is reflected by a sclera of the eye as a baseline image for macular pigments optical density measurement, the first region of the eye includes a foveal area or a part of a macula of the eye, the second region of the eye includes a perifoveal area or a part of a peripheral retina of the eye, the second spectroscopic technique is fundus reflection (FR) in which an intensity is measured for return light that is reflected by a sclera of the eye, amount of the one or more macular pigments is a macular pigment optical density (MPOD) or a macular pigment optical volume (MPOV), the fluorescing pigment is lipofuscin, the other pigments include at least one of melanin or hemoglobin, and the one or more macular pigments include at least one of a carotenoid, lutein, zeaxanthin, or meso-zeaxanthin.

Aspect 38. The non-transitory computer-readable storage medium of aspect 37, wherein the first fluorescence value and the second fluorescence value are measured by filtering fluorescent light from the eye using a high-pass filter that attenuates wavelengths shorter than a fluorescence wavelength of the fluorescing pigment Aspect 39. The non-transitory computer-readable storage medium of aspect 35, wherein: the first wavelength is within an absorption band of the fluorescing pigment and within an absorption band of the one or more macular pigments, and the first wavelength is within a wavelength range of about 480 nm to about 520 nm.

Aspect 40. The non-transitory computer-readable storage medium of aspect 35, wherein: the second wavelength is outside of an absorption band of the fluorescing pigment and outside an absorption band of the one or more macular pigments, and the first wavelength is in a wavelength range of about 600 nm to about 900 nm.

Aspect 41. The non-transitory computer-readable storage medium of aspect 35, wherein the instructions cause the computer to determine the amount of the one or more macular pigments by causing the computing apparatus to: calculate a difference between a first optical density and a second optical density, the first optical density including a logarithm of a ratio between the second fluorescence value and the first fluorescence, and the second optical density representing difference between the absorption values or the logarithm of a ratio between intensities for the absorption values.

Aspect 42. The non-transitory computer-readable storage medium of aspect 41, wherein the instructions cause the computer to calculate the difference between the first optical density and the second optical density by causing the computing apparatus to: calculate the first optical density, which is a fundus autofluorescence (FAF) optical density, according to:

$$OD_{FAF} = K \times \text{Log} \left( \frac{I_{per}}{I_{mac}} \right)_{\lambda_1},$$

wherein $OD_{FAF}$ is the FAF optical density, K is a predefined constant relating a first extinction coefficient at a peak wavelength of an absorption band and a second extinction coefficient at the first wavelength, $I_{per}$ is an intensity or irradiance of fluorescent light from a peripheral retina of the eye, $I_{mac}$ is the intensity or irradiance of fluorescent light from a macula of the eye, and $\lambda_1$ is the first wavelength; and calculate the second optical density, which is a fundus reflection (FR) optical density, according to:

$$OD_{FR} = \frac{a}{2} \times \text{Log} \left( \frac{I_{per}}{I_{mac}} \right)_{\lambda_2},$$

wherein $OD_{FR}$ is the FR optical density, a is a predefined constant relating a first absorption coefficient of the other pigments at the second wavelength to a second absorption coefficient of the other pigments at the first wavelength, $I_{per}$ is the intensity or irradiance of reflected light at the second wavelength from a peripheral retina of the eye, $I_{mac}$ is the intensity or irradiance of reflected light at the second wavelength from a macula of the eye, and $\lambda_2$ is the second wavelength.

Aspect 43. The non-transitory computer-readable storage medium of aspect 35, wherein the instructions further cause the computer to: generate, based on the amount of the one or more macular pigments, an image that represents a density of the one or more macular pigments with respect to position on a retina of the eye.

Aspect 44. The non-transitory computer-readable storage medium of aspect 35, wherein the instructions further cause the computer to: determine a correction factor for cataracts; and apply the correction factor to the amount of the one or more macular pigments to provide a corrected amount of the one or more macular pigments.

Aspect 45. The non-transitory computer-readable storage medium of aspect 44, wherein the instructions cause the computing apparatus to determine the correction factor by causing the computer to: determine the correction factor by calculating the correction factor based on vein extinction coefficients in a fundus autofluorescence (FAF) image and a fundus reflection (FR) image in accordance with $$A = \frac{\varepsilon_{FAF}}{\varepsilon_{FR}},$$

wherein A is the correction factor, $\varepsilon_{FAF}$ is an FAF extinction coefficient, and $\varepsilon_{FR}$ is an FR extinction coefficient.

Aspect 46. The non-transitory computer-readable storage medium of aspect 44, wherein the instructions further cause the computer to: use the amount of the one or more macular pigments to promote ocular health or to determine a treatment for treating a patient for age-related macular degeneration (AMD) or retinitis pigmentosa.

Aspect 47. The non-transitory computer-readable storage medium of aspect 44, wherein the instructions cause the computing apparatus to determine the amount of the one or more macular pigments by causing the computer to: wherein the instructions cause the computing apparatus to determine the amount of the one or more macular pigments by configuring the computing apparatus to: measure vein-extinction coefficients for both the first spectroscopic technique and the second spectroscopic technique; calculate the correction factor based on a ratio of a vein extinction coefficients between the first spectroscopic technique and the second spectroscopic technique, and apply the correction factor includes using the correction factor to adjust the amount of the one or more macular pigments, thereby compensating for cataract-related degradation.

Aspect 48. The non-transitory computer-readable storage medium of aspect 35, wherein the instructions further cause the computer to: store, in a medical database, the amount of the one or more macular pigments in association a patient; and analyze the amount of the one or more macular pigments using a longitudinal tracking analysis to monitor cataract progression of the patient with respect to time.

Aspect 49. The non-transitory computer-readable storage medium of aspect 35, wherein the instructions further cause the computer to: dynamically adjust an intensity of a one or more light sources irradiating the eye for the first spectroscopic technique based on a retinal reflectance of the eye, the intensity being dynamically adjusted to optimize signal-to-noise ratios for the first fluorescence value and/or the second fluorescence value.

Aspect 50. The non-transitory computer-readable storage medium of aspect 49, wherein the instructions further cause the computer to: dynamically adjust the intensity of another light source irradiating the eye for the second spectroscopic technique based on a retinal reflectance of the eye, the intensity of the another light source being dynamically adjusted to optimize a signal-to-noise ratio for one or more of the measure absorptions.

Aspect 51. The non-transitory computer-readable storage medium of aspect 35, wherein the instructions further cause the computer to: use the amount of the one or more macular pigments to determine raw macular pigment optical density (MPOD) values and corrected MPOD values; and cause a display to display a user interface for patient monitoring and management, the user interface being configured to display the raw MPOD value together with the corrected MPOD values alongside one or more graphical representations of a macular pigment distribution and one or more density changes with respect to time.

Aspect 52. Dual Light Source Implementation: The technique leverages two distinct light sources of varying wavelengths, directing light from both sources onto the macular tissue to evaluate macular pigment levels.

Aspect 53. First Light Source Application: The initial light source, with wavelengths spanning both the absorption bands of macular pigment and lipofuscin, facilitates attenuation by the former, consequently inducing lipofuscin fluorescence. This wavelength range (e.g., 480 nm-520 nm) is critical for the autofluorescence component of the method. In this approach a barrier filter blocks the crystalline lens autofluorescence, which its spectral emission could be 600 nm or longer but not limited to.

Aspect 54. Second Light Source Application: The wavelength of the second light source, designed to fall outside the absorption bands of lipofuscin and macular pigment, neither stimulates macular pigment nor triggers lipofuscin fluorescence. It may, however, be absorbed by other pigments such as melanin, serving as the baseline for the reflection imaging aspect of the method. This wavelength typically ranges from 600 nm to 900 nm, but not limited to that range.

Aspect 55. Accurate Macular Pigment Quantification: Leveraging the lipofuscin emission intensities in both the macula and peripheral retina to form an autofluorescence image, in conjunction with the light reflected by the sclera passing through the macula and peripheral retina for a baseline image, enables the measurement of macular pigment levels in the macular tissue with unparalleled precision.

Aspect 56. First light source to generate fundus autofluorescence: Wherein the lipofuscin absorption band and the wavelength of the first light source overlap, e.g., from 480 nm-520 nm, but not limited to.

Aspect 57. Second light source to generate fundus reflection image as a baseline image: The baseline measurement uses the reflection picture from the second light source, which does not overlap with standard pigments and lipofuscin, e.g., from 600 nm-900 nm, but not limited to.

Aspect 58. Construction of Macular Pigment Optical Images: The method synthesizes images of the macular pigment optical density (MPOD) and macular pigment optical volume (MPOV) using the fluorescence of the retinal pigment epithelium and the reflection of the retina.

Aspect 59. Formula for Macular Pigment Calculation: The technique employs the following formula for calculating macular pigment levels:

$$MPOD = \left[ K \cdot \log\left(I^{per}/I^{mac}\right)_{490\,nm} - 1/2\, a \cdot \left(\log\left(I^{per}/I^{mac}\right)_{650\,nm}\right]_{x,y} \right.$$

In this equation, "a" is a coefficient that compensates for the optical density of any pigment other than macular pigment in the retina in the spectral location of the macular pigment's maximum optical density (approximately 450-460 nm). Notably, the deployment of wavelengths is not confined to these specific ranges.

Aspect 60. Also in another version of the above equation, we can correct melanin in the place of 490 nm and then apply the correction factor on the whole equation:

$$MPOD = K \cdot \left[ \text{Log}\left(I_{per}/I_{mac}\right)_{490\,nm} - 1/2\, b \cdot \left(\log\left(I_{per}/I_{mac}\right)_{650\,nm}\right]_{x,y} \right.$$

Here b is the correction factor for the melanin absorption in the place 490 nm. Here K is applied to the whole equation.

Aspect 61. Flexibility and Adaptability: This technique demonstrates versatility and can be adapted to various scenarios and requirements in the quantification of macular pigments, reflecting a profound understanding of the underlying principles and a sophisticated approach to optical analysis.

Aspect 62. A method for correcting cataract-induced image degradation in bimodal imaging systems, which includes:

Measuring the vein extinction coefficients in both Fundus Autofluorescence (FAF) and Fundus Reflection (FR) images.

Calculating a correction factor A based on the ratio of vein extinction coefficients between FAF and FR images.

Utilizing the correction factor A to adjust the Macular Pigment Optical Density (MPOD) measurements to compensate for cataract-related degradation.

Aspect 63. The method as described in aspect 52, where the FAF image is obtained using an excitation wavelength of approximately 490 nm and an emission wavelength range of 650-750 nm.

Aspect 64. The method as described in aspect 52, where the FR image is obtained using an illumination wavelength of approximately 650 nm, thereby allowing for a double pass of light through the retina.

Aspect 65. The method as described in aspect 52, wherein A is determined through the following formula:

$A = \varepsilon_{FAF}/\varepsilon_{FR}$, where $\varepsilon_{FAF}$ and $\varepsilon_{FR}$ represent the vein extinction coefficients in the FAF and FR images, respectively.

Aspect 66. The method as described in aspect 52, further including a step to compare the calculated A against a predetermined threshold to assess the severity of the cataract-induced degradation.

Aspect 67. The method as described in aspect 52, where the correction factor A is applied to both Macular Pigment Optical Density (MPOD) and Macular Pigment Optical Volume (MPOV) values.

Aspect 68. The method as described in aspect 52, where the procedure is part of a larger multimodal imaging system that also measures levels of other retinal pigments such as melanin and hemoglobin.

Aspect 69. A bimodal imaging system designed to implement the method described in aspect 52, comprising:

Two distinct light sources, one for generating the FAF image and another for the FR image.

A data processing unit capable of calculating A and applying it as a correction factor to MPOD measurements.

Aspect 70. The method as described in aspect 52, where the calculated A is stored in a patient database to allow for longitudinal tracking of cataract progression over time.

Aspect 71. A computer program product that includes a non-transitory computer-readable medium with instructions stored thereon. When executed by a processor, these instructions cause the processor to perform the method as described in any one of aspects 52-71.

Aspect 72. A method for correcting Macular Pigment Optical Density (MPOD) measurements in the presence of cataracts, as described in any one of aspects 52-57, comprising the step of: Calculating a corrected MPOD (MPOD corrected) using the equation:

$$MPOD_{corrected} = MPOD_{measured} \times A$$

Aspect 73. The method as described in aspect 56, where A is calculated based on the vein extinction coefficients in both Autofluorescence Image (FAF) and Fundus Reflection (FR) images, using the formula: $A=\varepsilon_{FAF}/\varepsilon_{FR}$.

Aspect 74. The method as described in aspect 56 where the corrected MPOD (MPOD$_{corrected}$) is used for more accurate diagnosis and monitoring of macular health, especially in the presence of cataracts.

Aspect 75. The method as described in aspect 56, where the corrected MPOD (MPOD$_{corrected}$) is stored in a patient database for longitudinal tracking alongside the calculated A to assess the progression of cataract and its impact on macular health over time.

What is claimed is:

1. A method of measuring macular pigments in an eye, the method comprising:

using a first spectroscopic technique at a first wavelength to measure a first fluorescence value from a fluorescing pigment in a first region of the eye and measure a second fluorescence value from the fluorescing pigment in a second region of the eye, the first region of the eye including a greater density of one or more macular pigments than the second region of the eye;

using a second spectroscopic technique at a second wavelength of light that is incident on the eye to measure absorptions in the first region of the eye and the second region of the eye due to other pigments than the fluorescing pigment and the one or more macular pigments, thereby providing absorption values; and determining an amount of the one or more macular pigments in the first region of the eye using the first fluorescence value, the second fluorescence value, and the absorption values.

2. The method of claim 1, wherein determining the amount of the one or more macular pigments includes using the measured absorptions to remove a value of absorption due to the other pigments from a determination of macular-pigment absorption.

3. The method of claim 1, wherein:

the first spectroscopic technique is fundus autofluorescence (AFA), the second spectroscopic technique is fundus reflection (FR) in which an intensity is measured for return light that is reflected by a sclera of the eye, which is used as a baseline image for a macular pigments optical density measurement, the first region of the eye includes a foveal area or a part of a macula of the eye, the second region of the eye includes a perifoveal area or a part of a peripheral retina of the eye, amount of the one or more macular pigments is a macular pigment optical density (MPOD) or a macular pigment optical volume (MPOV), the fluorescing pigment is lipofuscin, the other pigments include at least one of melanin or hemoglobin, and the one or more macular pigments include at least one of a carotenoid, lutein, zeaxanthin, or meso-zeaxanthin.

4. The method of claim 3, wherein the first fluorescence value and the second fluorescence value are measured by filtering fluorescent light from the eye using a high-pass filter that attenuates wavelengths shorter than a fluorescence wavelength of the fluorescing pigment.

5. The method of claim 1, wherein:

the first wavelength is within an absorption band of the fluorescing pigment and within an absorption band of the one or more macular pigments, and the first wavelength is within a wavelength range of about 480 nm to about 520 nm.

6. The method of claim 1, wherein:

the second wavelength is outside of an absorption band of the fluorescing pigment and outside an absorption band of the one or more macular pigments, and the second wavelength is in a wavelength range of about 600 nm to about 900 nm.

7. The method of claim 1, wherein determining the amount of the one or more macular pigments further includes:

calculating a difference between a first optical density and a second optical density, the first optical density including a logarithm of a ratio between the second fluorescence value and the first fluorescence value, and the second optical density representing a difference between the absorption values or the logarithm of a ratio between intensities for the absorption values.

8. The method of claim 7, wherein calculating the difference between the first optical density and the second optical density includes:

calculating the first optical density, which is a fundus autofluorescence (FAF) optical density, according to:

$$OD_{FAF} = K \times Log \left( \frac{I_{per}}{I_{mac}} \right)_{\lambda_1},$$

wherein $OD_{FAF}$ is the FAF optical density, K is a predefined constant relating a first extinction coefficient at a peak wavelength of an absorption band and a second extinction coefficient at the first wavelength, $I_{per}$ is an intensity or irradiance of fluorescent light from a peripheral retina of the eye, $I_{mac}$ is the intensity or irradiance of fluorescent light from a macula of the eye, and $\lambda_1$ is the first wavelength; and calculating the second optical density, which is a fundus reflection (FR) optical density, according to:

$$OD_{FR} = \frac{a}{2} \times Log \left( \frac{I_{per}}{I_{mac}} \right)_{\lambda_2},$$

wherein $OD_{FR}$ is the FR optical density, a is another predefined constant relating a first absorption coefficient of the other pigments at the second wavelength to a second absorption coefficient of the other pigments at the first wavelength, $I_{per}$ is the intensity or irradiance of reflected light at the second wavelength from the peripheral retina of the eye, $I_{mac}$ is the intensity or irradiance of the reflected light at the second wavelength from the macula of the eye, and $\lambda_2$ is the second wavelength.

9. The method of claim 1, further comprising:
generating, based on the amount of the one or more macular pigments, an image that represents a density of the one or more macular pigments with respect to position on a retina of the eye.

10. The method of claim 1, further comprising:
determining a correction factor for cataracts; and
applying the correction factor to the amount of the one or more macular pigments to provide a corrected amount of the one or more macular pigments.

11. The method of claim 10, wherein the correction factor is calculated based on blood extinction coefficients in arteries or veins in a fundus autofluorescence (FAF) image and fundus reflection (FR) image in accordance with $$A = \frac{\varepsilon_{FAF}}{\varepsilon_{FR}},$$

wherein A is the correction factor, $\varepsilon_{FAF}$ is a first blood extinction coefficient in an FAF image, and $\varepsilon_{FR}$ is a second blood extinction coefficient in an FR image.

12. The method of claim 10, further comprising:
using the amount of the one or more macular pigments to determine a treatment for treating a patient for age-related macular degeneration (AMD) or retinitis pigmentosa.

13. The method of claim 10, wherein determining the correction factor for the cataracts includes:
measuring vein-extinction coefficients for both the first spectroscopic technique and the second spectroscopic technique;
calculating the correction factor based on a ratio of blood extinction coefficients extinction coefficients in arteries or veins between the first spectroscopic technique and the second spectroscopic technique, and
applying the correction factor includes using the correction factor to adjust the amount of the one or more macular pigments, thereby compensating for cataract-related degradation.

14. The method of claim 1, further comprising:
storing, in a medical database, the amount of the one or more macular pigments in association with a patient; and
analyzing the amount of the one or more macular pigments using a longitudinal tracking analysis to monitor cataract progression of the patient with respect to time.

15. The method of claim 1, further comprising:
dynamically adjusting an intensity of one or more light sources irradiating the eye for the first spectroscopic technique based on a retinal reflectance of the eye, the intensity being dynamically adjusted to optimize signal-to-noise ratios for the first fluorescence value and/or the second fluorescence value.

16. The method of claim 15, further comprising:
dynamically adjusting the intensity of another light source irradiating the eye for the second spectroscopic technique based on a retinal reflectance of the eye, the intensity of the another light source being dynamically adjusted to optimize a signal-to-noise ratio for one or more of the measured absorptions.

17. The method of claim 1, further comprising:
using the amount of the one or more macular pigments to determine raw macular pigment optical density (MPOD) values and corrected MPOD values; and
causing a display to display a user interface for patient monitoring and management, the user interface being configured to display a raw MPOD value together with the corrected MPOD values alongside one or more graphical representations of a macular pigment distribution and one or more density changes with respect to time.

18. A computing apparatus comprising:
one or more processors; and
a memory storing instructions that, when executed by the one or more processors, configure the computing apparatus to:
use a first spectroscopic technique at a first wavelength to measure a first fluorescence value from a fluorescing pigment in a first region of an eye and measure a second fluorescence value from the fluorescing pigment in a second region of the eye, the first region of the eye includes a greater density of one or more macular pigments than the second region of the eye;
use a second spectroscopic technique at a second wavelength of light that is incident on the eye to measure absorptions in the first region of the eye and the second region of the eye due to other pigments than the fluorescing pigment and the one or more macular pigments, thereby providing absorption values; and
determine an amount of the one or more macular pigments in the first region of the eye using the first fluorescence value, the second fluorescence value, and the absorption values.

19. The computing apparatus of claim 18, wherein the instructions cause the computing apparatus to determine the amount of the one or more macular pigments by configuring the computing apparatus to:
wherein determining the amount of the one or more macular pigments includes using the measured absorptions to remove a value of absorption due to the other pigments from a determination of macular-pigment absorption.

20. The computing apparatus of claim 18, wherein:
the first spectroscopic technique is fundus autofluorescence (AFA),
the second spectroscopic technique is fundus reflection (FR) in which an intensity is measured for return light that is reflected by a sclera of the eye,
the first region of the eye includes a foveal area or a part of a macula of the eye,
the second region of the eye includes a perifoveal area or a part of a peripheral retina of the eye,
amount of the one or more macular pigments is a macular pigment optical density (MPOD) or a macular pigment optical volume (MPOV),
the fluorescing pigment is lipofuscin,
the other pigments include at least one of melanin or hemoglobin, and
the one or more macular pigments include at least one of a carotenoid, lutein, zeaxanthin, or meso-zeaxanthin.

21. A non-transitory computer-readable storage medium, the computer-readable storage medium including instructions that when executed by a computer, cause the computer to:

using a first spectroscopic technique at a first wavelength to measure a first fluorescence value from a fluorescing pigment in a first region of an eye and measure a second fluorescence value from the fluorescing pigment in a second region of the eye, the first region of the eye includes a greater density of one or more macular pigments than the second region of the eye;

using a second spectroscopic technique at a second wavelength of light that is incident on the eye to measure absorptions in the first region of the eye and the second region of the eye due to other pigments than the fluorescing pigment and the one or more macular pigments, thereby providing absorption values; and determine an amount of the one or more macular pigments in the first region of the eye using the first fluorescence value, the second fluorescence value, and the absorption values.

22. The non-transitory computer-readable storage medium of claim 21, wherein:

the first spectroscopic technique is fundus autofluorescence (AFA), the second spectroscopic technique is fundus reflection (FR) in which an intensity is measured for return light that is reflected by a sclera of the eye, the first region of the eye includes a foveal area or a part of a macula of the eye, the second region of the eye includes a perifoveal area or a part of a peripheral retina of the eye, the second spectroscopic technique is fundus reflection (FR) in which an intensity is measured for return light that is reflected by a sclera of the eye, amount of the one or more macular pigments is a macular pigment optical density (MPOD) or a macular pigment optical volume (MPOV), the fluorescing pigment is lipofuscin, the other pigments include at least one of melanin or hemoglobin, and the one or more macular pigments include at least one of a carotenoid, lutein, zeaxanthin, or meso-zeaxanthin.

* * * * *